United States Patent
Mayse et al.

(10) Patent No.: US 11,103,684 B2
(45) Date of Patent: Aug. 31, 2021

(54) SYSTEMS, DEVICES, AND METHODS FOR TREATING A PULMONARY DISORDER WITH AN AGENT

(71) Applicant: Holaira, Inc., Plymouth, MN (US)

(72) Inventors: Martin L. Mayse, Wayzata, MN (US); Steven P. Mertens, Plymouth, MN (US)

(73) Assignee: Nuvaira, Inc., Plymouth, MN (US)

( * ) Notice: Subject to any disclaimer, the term of this patent is extended or adjusted under 35 U.S.C. 154(b) by 0 days.

(21) Appl. No.: 14/776,998

(22) PCT Filed: Mar. 14, 2014

(86) PCT No.: PCT/US2014/028063
§ 371 (c)(1),
(2) Date: Sep. 15, 2015

(87) PCT Pub. No.: WO2014/143898
PCT Pub. Date: Sep. 18, 2014

(65) Prior Publication Data
US 2016/0038725 A1 Feb. 11, 2016

Related U.S. Application Data

(60) Provisional application No. 61/799,642, filed on Mar. 15, 2013, provisional application No. 61/870,373, filed on Aug. 27, 2013.

(51) Int. Cl.
*A61M 25/10* (2013.01)
*A61M 29/02* (2006.01)
(Continued)

(52) U.S. Cl.
CPC ........... *A61M 29/02* (2013.01); *A61K 31/045* (2013.01); *A61K 31/05* (2013.01); *A61K 31/138* (2013.01);
(Continued)

(58) Field of Classification Search
CPC .... A61M 2025/105; A61M 2025/1086; A61M 25/104; A61M 2025/1075
See application file for complete search history.

(56) References Cited

U.S. PATENT DOCUMENTS 5,188,632 A * 2/1993 Goldenberg ....... A61B 1/00165
385/142
5,336,178 A 8/1994 Kaplan et al.
(Continued)

FOREIGN PATENT DOCUMENTS

WO WO 2004/093914 A1 11/2004
WO WO 2011060200 A1 * 5/2011 ......... A61B 18/1492

OTHER PUBLICATIONS

"Medication." Merriam-Webster.com. Merriam-Webster, n.d. Web. Jul. 20, 2017.*
(Continued)

*Primary Examiner* — Nathan R Price
*Assistant Examiner* — Courtney B Fredrickson
(74) *Attorney, Agent, or Firm* — Patterson Thuente Pedersen, P.A.

(57) ABSTRACT

A medication delivery device for treatment of a pulmonary disorder in a patient includes an elongate member, an expandable member is coupled to a distal end of the elongate member, and an agent delivery portion coupled to an external surface of the expandable member. The agent delivery portion includes an agent that disrupts nerve activity.

37 Claims, 15 Drawing Sheets

Figure 1:
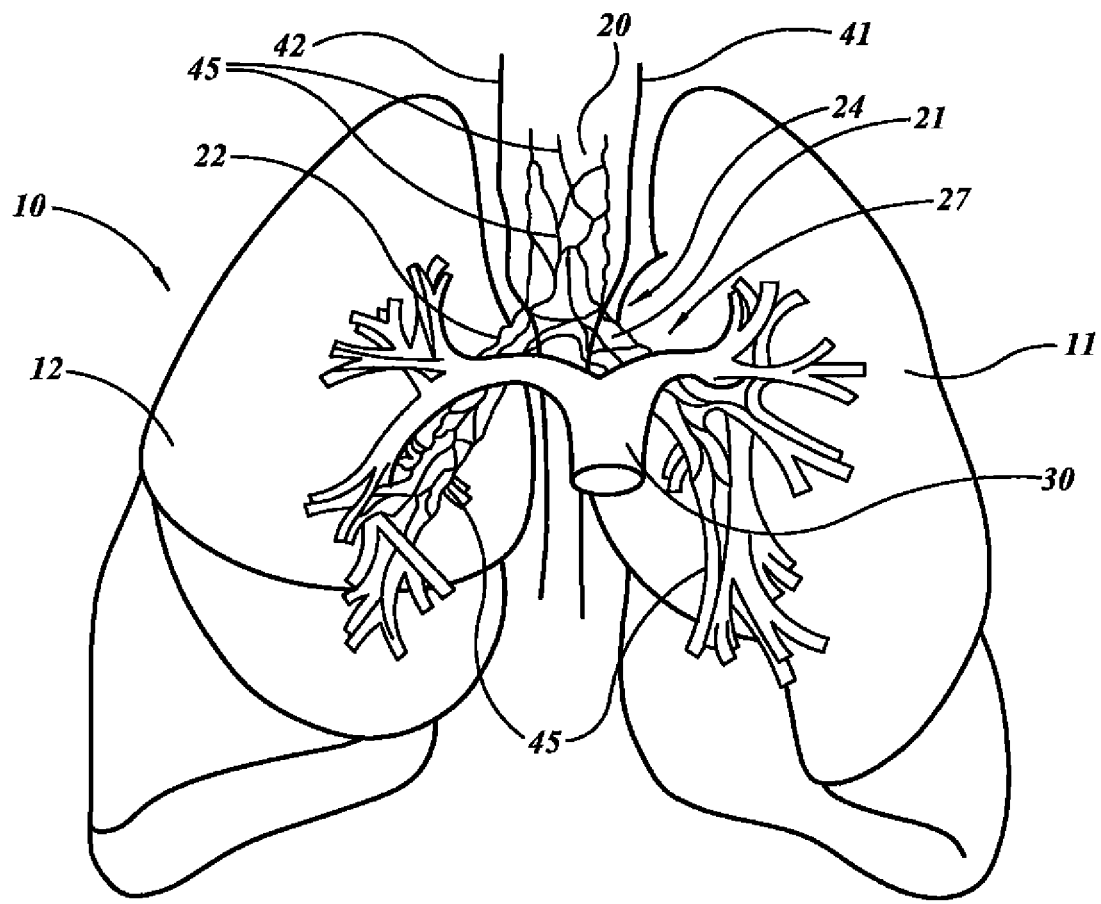

(51) Int. Cl.

| | | |
|---|---|---|
| *A61L 31/16* | (2006.01) | |
| *A61K 31/167* | (2006.01) | |
| *A61K 31/138* | (2006.01) | |
| *A61K 31/045* | (2006.01) | |
| *A61K 31/185* | (2006.01) | |
| *A61K 33/00* | (2006.01) | |
| *A61K 31/14* | (2006.01) | |
| *A61K 31/436* | (2006.01) | |
| *A61K 31/7004* | (2006.01) | |
| *A61K 31/05* | (2006.01) | |
| *A61K 31/201* | (2006.01) | |
| *A61K 31/445* | (2006.01) | |
| *A61K 31/166* | (2006.01) | |
| *A61K 31/191* | (2006.01) | |
| *A61L 29/16* | (2006.01) | |
| *A61K 38/17* | (2006.01) | |
| *A61K 33/36* | (2006.01) | |

(52) U.S. Cl.
CPC ............ *A61K 31/14* (2013.01); *A61K 31/166* (2013.01); *A61K 31/167* (2013.01); *A61K 31/185* (2013.01); *A61K 31/191* (2013.01); *A61K 31/201* (2013.01); *A61K 31/436* (2013.01); *A61K 31/445* (2013.01); *A61K 31/7004* (2013.01); *A61K 33/00* (2013.01); *A61K 33/36* (2013.01); *A61K 38/1732* (2013.01); *A61K 38/1735* (2013.01); *A61L 29/16* (2013.01); *A61L 31/16* (2013.01); *A61M 25/104* (2013.01); *A61L 2300/402* (2013.01); *A61M 2025/105* (2013.01); *A61M 2025/1086* (2013.01)

(56) References Cited

U.S. PATENT DOCUMENTS

| | | | |
|---|---|---|---|
| 5,624,392 A * | 4/1997 | Saab ................. | A61F 7/123 604/113 |
| 5,642,730 A | 7/1997 | Baran | |
| 5,766,605 A | 6/1998 | Sanders et al. | |
| 5,833,707 A * | 11/1998 | McIntyre ............. | A61F 2/92 606/108 |
| 6,299,633 B1 | 10/2001 | Laufer | |
| 6,488,673 B1 | 12/2002 | Laufer et al. | |
| 6,526,976 B1 | 3/2003 | Baran | |
| 6,955,661 B1 | 10/2005 | Herweck et al. | |
| 7,608,275 B2 | 10/2009 | Deem et al. | |
| 8,088,127 B2 | 1/2012 | Mayse et al. | |
| 8,133,497 B2 | 3/2012 | Deem et al. | |
| 8,172,827 B2 | 5/2012 | Deem et al. | |
| 8,226,638 B2 | 7/2012 | Mayse et al. | |
| 8,338,164 B2 | 12/2012 | Deem et al. | |
| 8,483,831 B1 | 7/2013 | Hlavka et al. | |
| 8,489,192 B1 | 7/2013 | Hlavka et al. | |
| 8,731,672 B2 | 5/2014 | Hlavka et al. | |
| 8,740,895 B2 | 6/2014 | Mayse et al. | |
| 8,777,943 B2 | 7/2014 | Mayse et al. | |
| 8,808,236 B2 * | 8/2014 | Orr ..................... | A61M 25/10 604/103.01 |
| 8,808,280 B2 | 8/2014 | Mayse et al. | |
| 8,821,489 B2 | 9/2014 | Mayse et al. | |
| 8,911,439 B2 | 12/2014 | Mayse et al. | |
| 8,932,289 B2 | 1/2015 | Mayse et al. | |
| 8,961,507 B2 | 2/2015 | Mayse et al. | |
| 8,961,508 B2 | 2/2015 | Mayse et al. | |
| 9,005,195 B2 | 4/2015 | Mayse et al. | |
| 9,017,324 B2 | 4/2015 | Mayse et al. | |
| 9,125,643 B2 | 9/2015 | Hlavka et al. | |
| 9,149,328 B2 | 10/2015 | Dimmer et al. | |
| 9,339,618 B2 | 5/2016 | Deem et al. | |
| 9,398,933 B2 | 7/2016 | Mayse | |
| 2002/0115991 A1 | 8/2002 | Edwards | |
| 2004/0220556 A1 | 11/2004 | Cooper et al. | |
| 2004/0226556 A1 | 11/2004 | Deem et al. | |
| 2004/0267195 A1 * | 12/2004 | Currlin ............... | A61F 2/958 604/103.1 |
| 2006/0225742 A1 | 10/2006 | Deem et al. | |
| 2007/0025919 A1 * | 2/2007 | Deem ................. | A61K 38/164 424/45 |
| 2008/0004596 A1 * | 1/2008 | Yun .................... | A61M 25/0084 604/508 |
| 2009/0264821 A1 * | 10/2009 | Mafi ................. | A61B 17/00491 604/103.01 |
| 2009/0306644 A1 | 12/2009 | Mayse et al. | |
| 2011/0118725 A1 | 5/2011 | Mayse et al. | |
| 2011/0152855 A1 | 6/2011 | Mayse et al. | |
| 2011/0257647 A1 | 10/2011 | Mayse et al. | |
| 2011/0301587 A1 | 12/2011 | Deem et al. | |
| 2012/0016358 A1 | 1/2012 | Mayse et al. | |
| 2012/0016363 A1 | 1/2012 | Mayse et al. | |
| 2012/0016364 A1 | 1/2012 | Mayse et al. | |
| 2012/0111324 A1 | 5/2012 | Kraft et al. | |
| 2012/0203216 A1 | 8/2012 | Mayse et al. | |
| 2012/0203222 A1 | 8/2012 | Mayse et al. | |
| 2012/0209261 A1 | 8/2012 | Mayse et al. | |
| 2012/0209296 A1 | 8/2012 | Mayse et al. | |
| 2012/0302909 A1 | 11/2012 | Mayse et al. | |
| 2012/0310233 A1 | 12/2012 | Dimmer et al. | |
| 2012/0316552 A1 | 12/2012 | Mayse et al. | |
| 2012/0316559 A1 | 12/2012 | Mayse et al. | |
| 2013/0123751 A1 | 5/2013 | Deem et al. | |
| 2013/0204068 A1 * | 8/2013 | Gnanashanmugam ................. | A61N 5/1002 600/1 |
| 2013/0289555 A1 | 10/2013 | Mayse et al. | |
| 2013/0289556 A1 | 10/2013 | Mayse et al. | |
| 2013/0296647 A1 | 11/2013 | Mayse et al. | |
| 2013/0303948 A1 | 11/2013 | Deem et al. | |
| 2013/0310822 A1 | 11/2013 | Mayse et al. | |
| 2013/0345700 A1 | 12/2013 | Hlavka et al. | |
| 2014/0186341 A1 | 7/2014 | Mayse | |
| 2014/0236148 A1 | 8/2014 | Hlavka et al. | |
| 2014/0257271 A1 | 9/2014 | Mayse et al. | |
| 2014/0276792 A1 | 9/2014 | Kaveckis et al. | |
| 2015/0051597 A1 | 2/2015 | Mayse et al. | |
| 2015/0141985 A1 | 5/2015 | Mayse et al. | |
| 2015/0150625 A1 | 6/2015 | Deem et al. | |
| 2015/0190193 A1 | 7/2015 | Mayse et al. | |
| 2015/0366603 A1 | 12/2015 | Hlavka et al. | |
| 2016/0022351 A1 | 1/2016 | Kaveckis et al. | |
| 2016/0038725 A1 | 2/2016 | Mayse et al. | |
| 2016/0192981 A1 | 7/2016 | Dimmer et al. | |
| 2018/0028748 A1 | 2/2018 | Deem et al. | |

OTHER PUBLICATIONS

PCT/ISA/210 International Search Report for PCT/US2014/028063, dated Aug. 27, 2014, 6 pages.
PCT/ISA/237 Written Opinion for PCT/US2014/028063, dated Aug. 27, 2014, 18 pages.
Application and File history for U.S. Appl. No. 15/728,172, filed Oct. 9, 2017. Inventors: Deem et al.

* cited by examiner

SYSTEMS, DEVICES, AND METHODS FOR TREATING A PULMONARY DISORDER WITH AN AGENT

RELATED APPLICATIONS

The present application is a National Phase entry of PCT Application No. PCT/US2014/028063, filed Mar. 13, 2014, which claims the benefit of U.S. Provisional Application No. 61/799,642 filed Mar. 15, 2013, and U.S. Provisional Application No. 61/870,373, filed Aug. 27, 2013, both of which are entitled "Systems, Devices, and Methods for Treating a Pulmonary Disorder with an Agent", said applications being herein incorporated in their entireties by reference.

BACKGROUND

Technical Field

The present invention generally relates to the field of treatment of the pulmonary diseases through the delivery of an agent to an airway of a patient.

Description of the Related Art

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include cough; breathlessness; and wheeze. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs, resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

A variety of solutions have been proposed for addressing pulmonary disorders, including COPD. One conventional treatment for COPD includes delivering the pharmaceutical drug tiotropium to the lungs via an inhaler. Typically, a patient places tiotropium capsules in a specially designed inhaler, and then breathes in dry powder contained in the capsules through the inhaler. This treatment must be administered on a recurring, sometimes daily, basis and its efficacy can be highly dependent on patient compliance.

Another conventional treatment includes maneuvering a catheter with an electrode to an affected area of the lungs and delivering thermal radiofrequency energy directly to the airway wall to directly heat the tissue and thereby reduce airway smooth muscle mass. This treatment, known as bronchial thermoplasty, requires patients to be treated over multiple sessions with each session targeting a different area of the lungs. Possible side-effects over the course of the treatments include asthma attacks, wheezing, chest discomfort, chest pain, partial collapse of the lungs, lower airway bleeding, anxiety, headaches, and nausea.

Several particularly effective treatments for pulmonary disorders are described in, for example, U.S. Pat. No. 8,088,127, titled, "Systems, Assemblies, and Methods for Treating a Bronchial Tree," and U.S. Patent Application Publication No. 2011/0152855, titled, "Delivery Devices With Coolable Energy Emitting Assemblies." In one example treatment described in these documents, a pulmonary treatment system delivers energy to damage a nerve trunk extending along a first airway of a patient, which thereby reduces airway resistance in a second airway distal to the first airway. This treatment provides numerous advantages over other, conventionally available treatments, including being far less invasive and requiring far fewer treatments.

BRIEF SUMMARY

It has been recognized that delivering an agent to an airway wall of a patient at a treatment location can affect nerves extending along the airway, thereby reducing airway obstruction in airways distal to the treatment location.

In one aspect, a medication delivery device for treatment of a pulmonary disorder in a patient includes an elongate member, an inflatable balloon coupled to a distal end of the elongate member, and an agent delivery portion coupled to an external surface of the inflatable balloon, the agent delivery portion including an agent that disrupts nerve activity, such as pulmonary nerve activity. In an embodiment, the inflatable balloon is configured to engage a wall of the airway when the balloon is in an inflated condition. The agent delivery portion is configured to be released from the external surface of the balloon, and absorbed into airway tissue to disrupt the nerve activity, and more particularly pulmonary nerve activity.

In some embodiments, the agent is intended to have a permanent effect on the nerves. In this case, the agent can be selected from a group of ribosome-inactivating proteins including ricin, abrin, and saporin. The agent can be selected from a group of agents consisting of phenol (3%), ropivacaine (also referred to as rINN, a local anesthetic that been shown to ablate nerve axons), sodium tetradecyl sulfate (STS) (1%-3%), polidocanol, ethanol (99.5%), sugar (hypertonic [50%] dextrose solution), ethanolamine oleate (5%), sodium morrhuate (5%), arsenic, nitric oxide, and glutonate.

In other examples, the agent is intended to have only a short term effect on the nerves. Such effects can be realized, for example, only while the agent delivery device, such as a drug eluting stent, is in place. In this case, the agent can be selected from a group consisting of lidocain, bupivacaine, mepivacaine, procainamide, mexiletine, tocainide, tetrodotoxin, tetraethylammonium, and chlorotoxin.

The balloon can be expandable to a size sufficient to bring an entire exposed surface of the agent delivery portion into direct contact with a body lumen at least 6 mm in diameter.

The exposed surface of the agent delivery portion can be a band that extends at least partially around a circumference of the balloon. The band can extend completely around the circumference of the balloon.

The agent delivery portion can be movable relative to the balloon. The agent delivery portion can be a ring that floats freely relative to the balloon.

The agent delivery portion can be a layer that directly coats a portion of the external surface of the balloon.

The balloon can be sized for treatment of a main stem bronchus or a lobar bronchus of an adult human between the ages of 21 and 58.

In another aspect, a medication delivery device for treatment of a pulmonary disorder in a patient includes an expandable member that includes a collapsed configuration for delivery to a treatment location in an airway of the patient and an expanded, treatment configuration in which an outside perimeter of the expandable member contacts an interior surface of the airway of the patient at the treatment location; and a medication delivery portion coupled to an exterior surface of the expandable member. The medication delivery portion can extend in a circumferential direction around the expandable member. The medication delivery portion can be sized to fit at least partially between two adjacent cartilage rings of the airway when the expandable member is in the expanded, treatment configuration. The medication delivery portion can include a medication that affects nerves that run along the airway so as to relieve airway obstruction in at least one airway distal to the treatment location.

In an embodiment, the medication can be configured to be released from the medication delivery portion when the expandable member is in the treatment configuration. In another embodiment, the medication can be configured to be released from the medication delivery portion when the expandable member is an air-filled environment. The medication in either embodiment can be configured to be absorbed by airway tissue to disrupt activity in the nerves.

The expandable member can be a basket that is configured for temporary deployment in the airway during treatment of the airway followed by withdrawal from the airway.

The expandable member can be a balloon. The medication delivery portion includes a raised portion of the balloon that includes a profile shaped to facilitate seating between the two adjacent cartilage rings. The medication delivery portion can be movable relative to the balloon to facilitate to facilitate seating between the two adjacent cartilage rings. The medication delivery portion can include a plurality of needles that extend radially outward from a surface of the balloon when the balloon is in the expanded, treatment configuration. The plurality of needles can be coated with the medication. The plurality of needles can be arranged around the circumference of the expandable member to preferentially target nerves located on a posterior side of the patient.

The expandable member can be a stent. The stent can be configured for permanent placement in the airway. The stent can be configured for temporary placement in the airway. The medication delivery portion can include a coating on struts of the stent. The medication delivery portion can include a covering that extends over struts of the stent. The medication delivery portion can include a raised portion that includes a profile shaped to facilitate engagement between the two adjacent cartilage rings. The raised portion can be movable relative to the stent to facilitate to facilitate seating between the two adjacent cartilage rings. The stent can include tapers on opposite ends that facilitate placement and retention in the airway of the patient.

The medication delivery device can further include a plurality of marking elements arranged on either side of the medication delivery portion to facilitate placement between the adjacent cartilage rings.

The agent can be selected from a group of ribosome-inactivating proteins including ricin, abrin, and saporin. The agent can be selected from a group of agents consisting of phenol (3%), ropivacaine (also referred to as rINN, a local anesthetic that been shown to ablate nerve axons), sodium tetradecyl sulfate (STS) (1%-3%), polidocanol, ethanol (99.5%), sugar (hypertonic [50%] dextrose solution), ethanolamine oleate (5%), sodium morrhuate (5%), arsenic, nitric oxide, and glutonate. The agent can be selected from a group consisting of lidocain, bupivacaine, mepivacaine, procainamide, mexiletine, tocainide, tetrodotoxin, tetraethylammonium, and chlorotoxin.

The expandable member can be sized for treatment of a main stem bronchus or a lobar bronchus of an adult human between the ages of 21 and 58.

In another aspect, a medication delivery system for treatment of a pulmonary disorder in a patient can include an elongate delivery device, and a medication delivery treatment device. The delivery device can include a lumen with an inside diameter ranging from 1.0 mm to 6.0 mm. The medication delivery treatment device includes an expandable member that includes a collapsed configuration for delivery through the lumen of the elongate delivery device to a treatment location in an airway of the patient and an expanded, treatment configuration in which an outside perimeter of the expandable member contacts an interior surface of the airway of the patient at the treatment location; and a medication delivery portion coupled to an exterior surface of the expandable member. The medication delivery portion includes a medication that affects nerves that run along the airway so as to relieve airway obstruction in at least one airway distal to the treatment location.

The elongate delivery device can be a flexible bronchoscope.

The expandable member can be an inflatable balloon. The expandable member can be a stent.

The medication delivery system can further include an elongate sheath including an outside diameter that is less than the inside diameter of the lumen of the flexible bronchoscope and an inside diameter that is greater than an outside diameter of the stent in the collapsed configuration.

The medication delivery system can further include a balloon dimensioned to expand the stent from the collapsed configuration to the expanded configuration.

The medication delivery system can further include a plurality of needles coupled to the medication delivery portion. Each of the needles can extend at least 2 mm radially beyond an external surface of the expandable member when the expandable member is in the expanded, treatment configuration.

Figure 9:
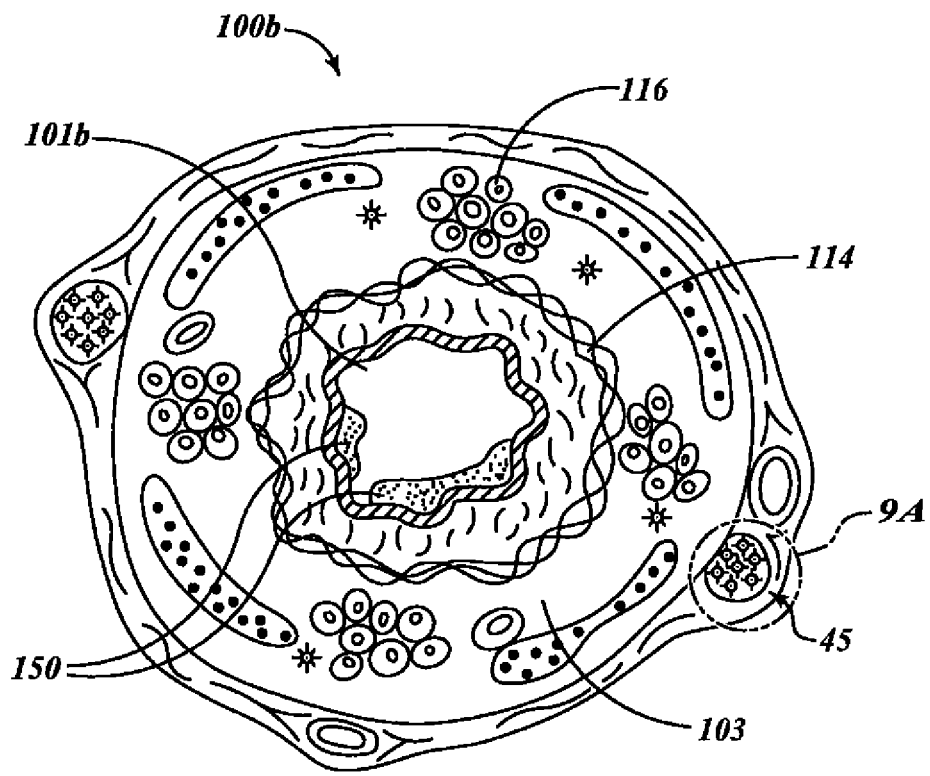
Figure 10:
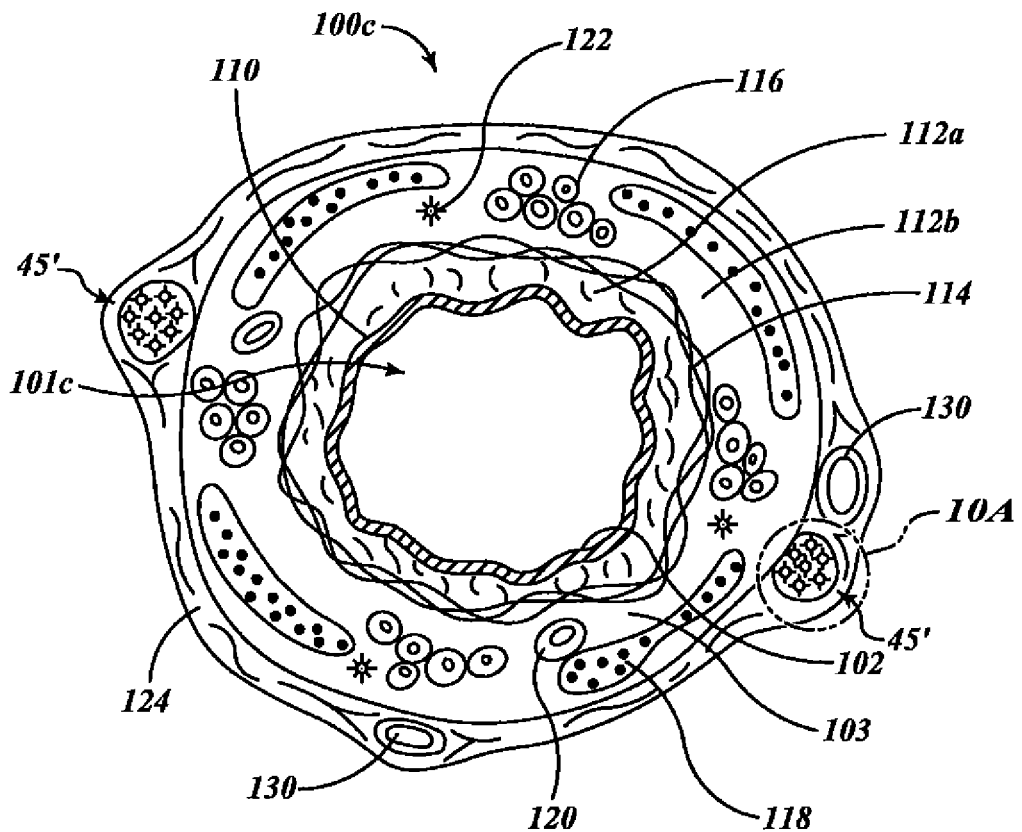

In another aspect, a method of delivering medication to an airway of a patient to treat a pulmonary disorder in the patient includes positioning a distal end of an elongate member in treatment location in an airway of the patient, the elongate member including a medication delivery device having an expandable member and a medication delivery portion; at least partially expanding the expandable member; and positioning the medication delivery portion at least partially or completely between two adjacent cartilage rings in an airway wall of the airway; maintaining the medication delivery portion in close contact with the airway wall of the airway while the medication delivery portion is positioned at least partially or entirely between the adjacent cartilage rings so that a medication in the medication delivery portion transfers into the airway wall to affect nerves that run along the airway so as to relieve airway obstruction in at least one airway distal to the treatment location.

The expandable member can be an inflatable balloon, and the at least partially expanding the expandable member include filling the balloon with a fluid.

The maintaining the medication delivery portion in close contact with the airway wall can include rotating the medication delivery portion between the adjacent cartilage rings. Rotating the medication delivery portion can include partially deflating the balloon, then rotating the medication delivery device using the adjacent cartilage rings as a guide, and then inflating the balloon.

Positioning the medication delivery portion between two adjacent cartilage rings can include viewing the medication delivery portion through the balloon with an optical element of bronchoscope positioned proximal of the balloon. Viewing the medication delivery portion through the balloon can include optically coupling the optical element of the bronchoscope to a proximal portion of the balloon.

Positioning the medication delivery portion between two adjacent cartilage rings can include viewing at least one marking element adjacent the medication delivery portion through the balloon with an optical element of bronchoscope positioned proximal of the balloon. Viewing the least one marking element through the balloon can include optically coupling the optical element of the bronchoscope to a proximal portion of the balloon.

Positioning a distal end of an elongate member in treatment location can include advancing the medication delivery device through a working channel of a flexible bronchoscope. The working channel of the flexible bronchoscope can include an inside diameter in the range of 1.0 mm to 6.0 mm.

The expandable member can be a stent, and the at least partially expanding the expandable member can include expanding the stent within the airway of the patient. The method can further include removing the stent from the airway following treatment. Removing the stent from the airway following treatment can include removing the stent between about one minute and about two years after placing the stent in the airway. Removing the stent from the airway following treatment can include removing the stent between about four months and eight months after placing the stent in the airway. Removing the stent from the airway following treatment can include removing the stent about six months after placing the stent in the airway.

Positioning the medication delivery portion between two adjacent cartilage rings can include moving the medication delivery portion relative to the expandable member.

The method can further include pressing a plurality of needles positioned on the medication delivery portion into the airway wall.

The expandable member can be a basket, and the at least partially expanding the expandable member can include expanding the basket in the airway.

In an embodiment, the nerves can comprise nerve trunks extending along an outer surface of the airway wall. In another embodiment, the nerves are disposed at least about 1 mm radially outward from an inner surface of the airway wall.

In a particular embodiment, the airway obstruction can be relieved in the airway that is distal to the treatment location without positioning the medication delivery portion in the airway that is distal to the treatment location.

BRIEF DESCRIPTION OF THE SEVERAL VIEWS OF THE DRAWINGS

The drawings discussed in the detailed description are described briefly as follows, in which:

FIG. 1 is an anterior view of the lungs, blood vessels, and nerves near to and in the lungs.

FIG. 2 is a further anterior view of the lungs in FIG. 1.

FIG. 3 is a cross-sectional view of a main stem bronchus between two adjacent cartilage rings, taken along line 3-3 of FIG. 2.

FIG. 4 is a cross-sectional view of a main stem bronchus through one of the cartilage rings, taken along line 4-4 of FIG. 2.

FIG. 5 is a cross-sectional view of a healthy distal airway in the lung, taken along line 5-5 of FIG. 2.

FIG. 6 is a cross-sectional view of the distal airway in FIG. 5 in which the airway is in an unhealthy constricted state, and mucus is in an airway lumen.

FIG. 7 is a schematic illustration of an agent delivery system during a treatment session according to one aspect.

FIG. 7A is a schematic illustration of the agent delivery system of FIG. 7 positioned within a left main bronchus according to one aspect.

FIGS. 8A and 8B are side elevation views of the agent delivery system of FIG. 7 positioned within an airway during treatment.

FIG. 9 is a cross-sectional view of a distal airway in the lung prior to treatment, taken along line 9-9 of FIG. 7.

FIG. 9A is a detail view of the nerve axons of a nerve trunk associated with the airway of FIG. 9.

FIG. 10 is a cross-sectional view of the distal airway of FIG. 9 after a treatment.

FIG. 10A is a detail view of the destroyed nerve axons of the nerve trunk associated with the airway of FIG. 10.

FIG. 11 is a side elevation view of an agent delivery system, according to another aspect, which includes features that facilitate positioning the agent delivery portion.

FIG. 12 is a side elevation view of an agent delivery system, according to another aspect, which includes an agent delivery portion that protrudes beyond a surface of the expandable member to act as a positioned.

FIG. 13 is a side elevation view of an agent delivery system, according to another aspect, which includes needles that project from the surface of the agent delivery portion.

FIG. 14 is a side elevation view of an agent delivery system, according to another aspect, in which the expandable member takes the form of an expandable and collapsible basket.

FIG. 15 is a side elevation view of an agent delivery system in the form of a stent according to another aspect.

FIG. 16 is a side elevation view of an agent delivery system in the form of a stent, according to another aspect, with a raised agent delivery portion.

FIG. 17 is a side elevation view of an agent delivery system in the form of a stent, according to another aspect, having tapered ends that facilitate placement in a bronchus.

DETAILED DESCRIPTION

FIGS. 1-6 provide an overview of human lung function and the role the nervous system can play in a diseased lung. FIGS. 7 and 8 provide an overview of an example treatment applied to the pulmonary system according to one aspect of the present disclosure. FIGS. 9 and 10 provide an overview of the effects of the treatment illustrated in FIGS. 7 and 8. FIGS. 11-17 illustrate further examples aspects of the present disclosure.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and a right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen-enriched blood then flows from the alveolar capillaries through the branching blood vessels of the pulmonary venous system to the heart. The heart pumps the oxygen-rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

The nervous system provides communication between the brain and the lungs 10 using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways are largely parasympathetic in nature and travel between the lung and the brain in the right vagus nerve 42 and the left vagus nerve 41.

Some of the nerve tissue in the network of nerve trunks 45 coalesce into other nerves (e.g., nerves connected to the esophagus, nerves though the chest and into the abdomen, and the like). Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways, as discussed in connection with FIGS. 3 and 4.

Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. While efferent nerve tissue innervates smooth muscle cells all the way from the trachea 20 to the terminal bronchioles, the afferent fiber innervation is largely limited to the trachea 20 and larger bronchi. There is a constant, baseline tonic activity of the efferent vagus nerve tissues to the airways which causes a baseline level of smooth muscle contraction and mucous secretion.

Figure 2:
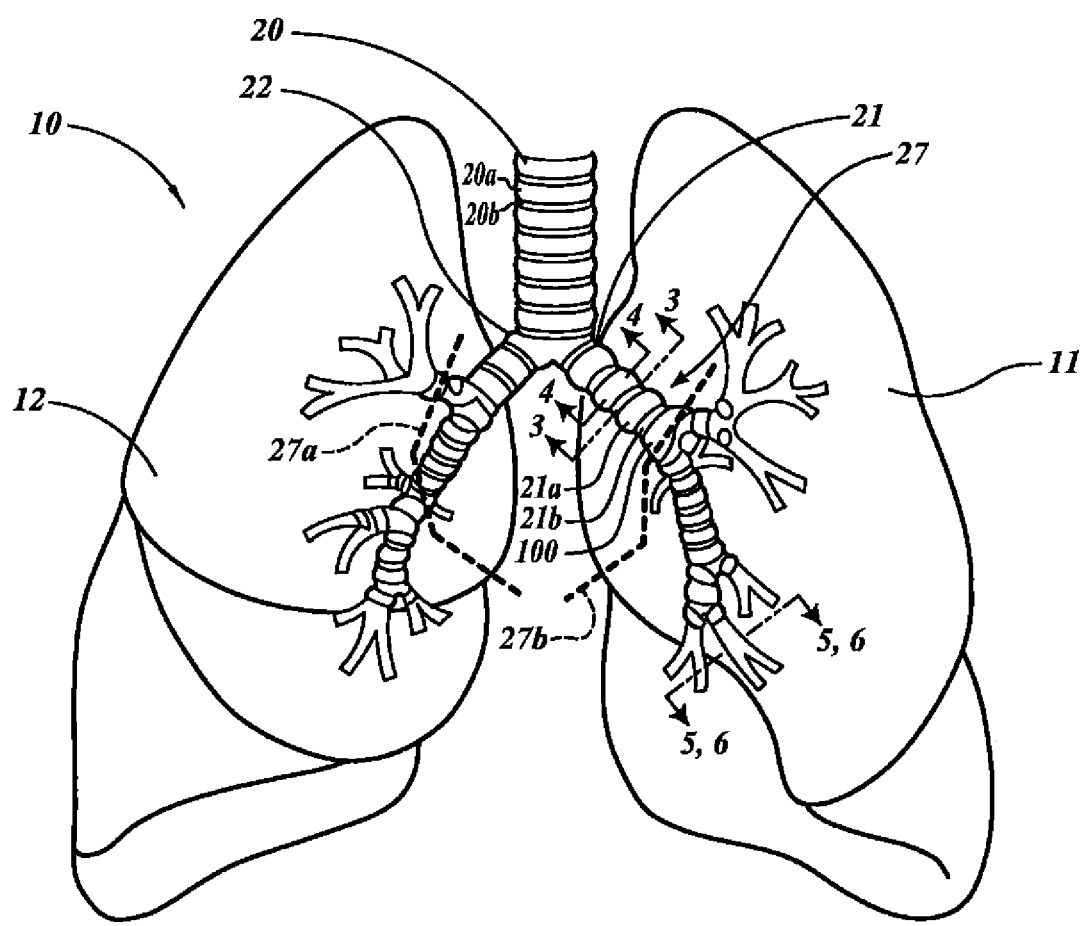

FIG. 2 is an anterior view of the lungs 10, 11; the trachea 20; and the bronchial tree 27. FIG. 2 includes a generalized illustration of the structure imposed by cartilage rings on the trachea 20 and bronchial tree 27. Portion 20a of the trachea 20 in FIG. 2 represents a portion of the trachea 20 that includes a cartilage ring, and portion 20b represents a portion of the trachea 20 between adjacent cartilage rings. Likewise, portion 21a represents a portion of the left main bronchus 21 that includes a cartilage ring, and portion 21b represents a portion of the left main bronchus 21 between adjacent cartilage rings. For ease of representation, the number of cartilage rings has been reduced and the spacing between the cartilage rings has been increased.

Notably, cartilage rings in the trachea do not extend around the entire circumference of the trachea, but instead are discontinuous on a posterior side of the trachea, which faces the esophagus. The discontinuity of the cartilage rings accommodates expansion of the esophagus into the tracheal space, for example, as food is swallowed. The shape of cartilage rings contributes to the cross-sectional shape of the trachea. Studies of the trachea have revealed a diversity of cross-sectional shapes in different patients, including elliptical, C-shaped, U-shaped, D-shaped, triangular, and circular. In addition, the cross-sectional shape of the trachea can change during the respiratory cycle from, for example, an elliptical shape during inspiration to, for example, a horse-shoe shape during exhalation.

Figure 3:
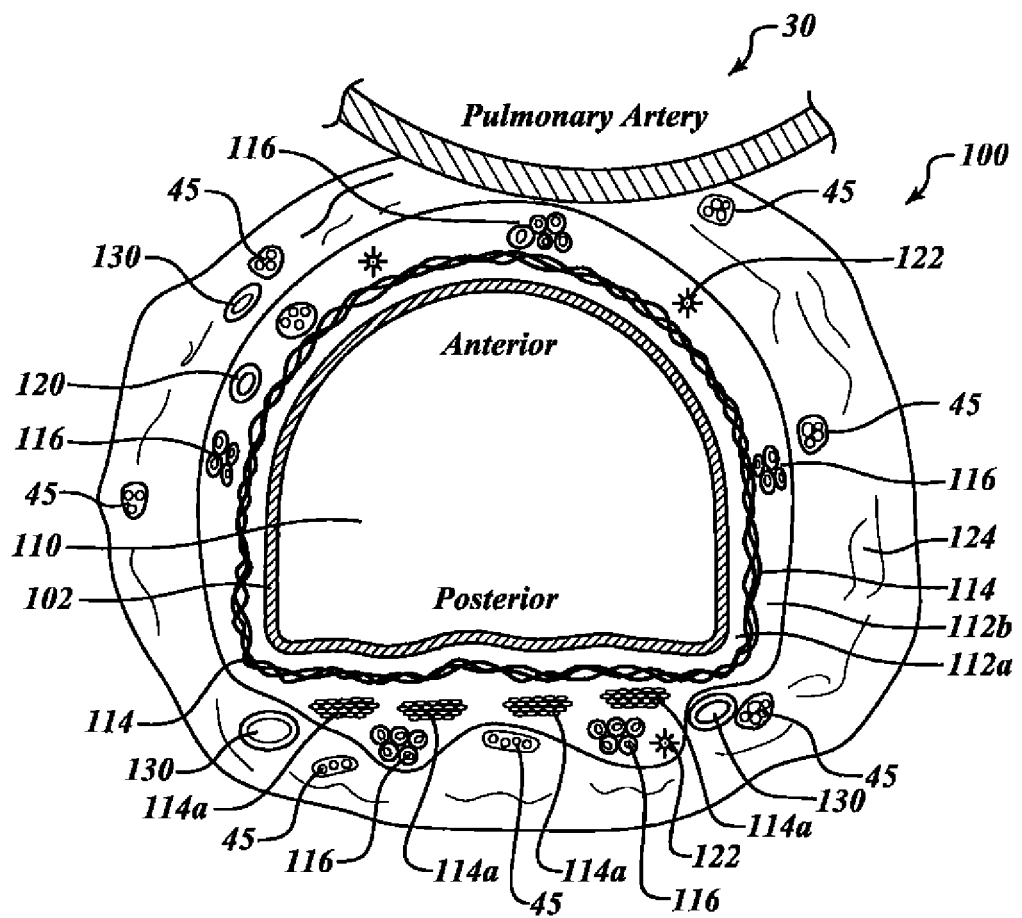
Figure 4:
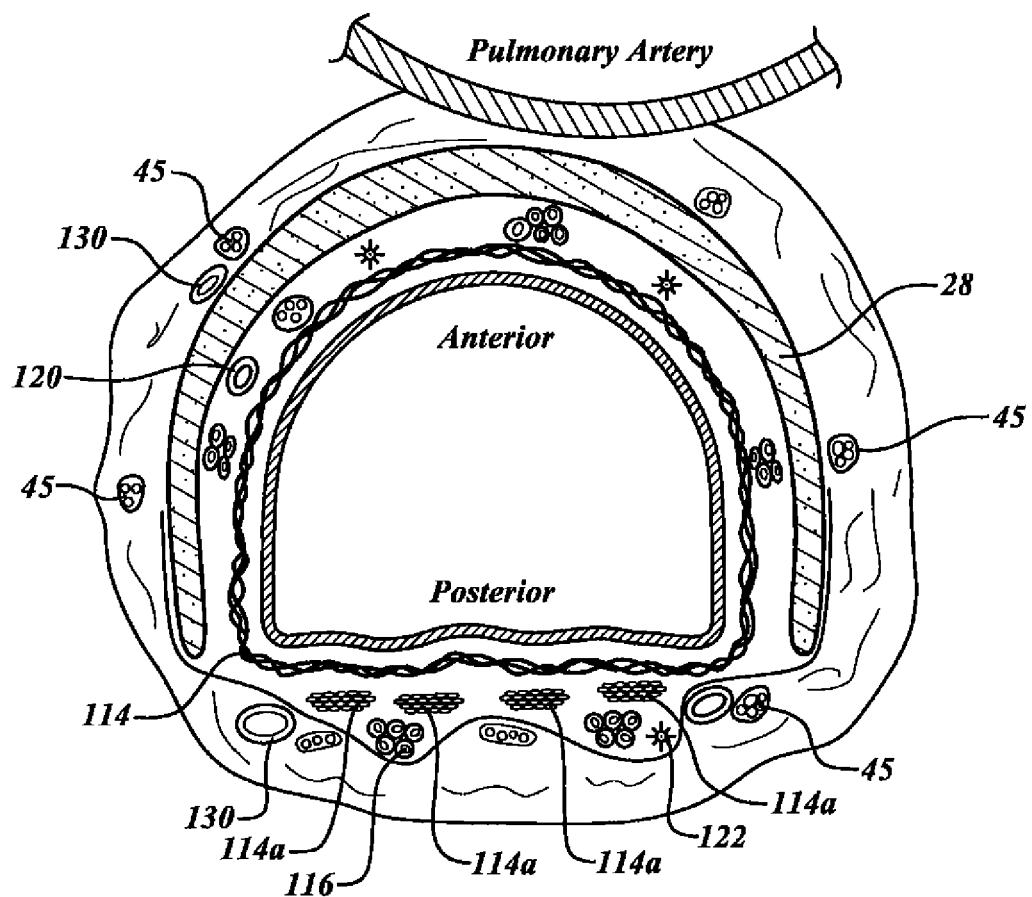

The cartilage rings in the left and right main bronchus are also incomplete. FIG. 3 is a cross-sectional view of a portion of an airway 100 in the left main bronchus 21 that is located between adjacent cartilage rings. FIG. 4 is a cross-sectional view of the airway 100 in portion of the left main bronchus 21 that includes a cartilage ring 28. In this example, the C-shaped cartilage ring 28 contributes to the D-shaped cross-sectional shape of the illustrated portion of the left main bronchus 21. The pulmonary artery 30 extends along an anterior side of the airway 100.

The airway 100 includes a lumen 101 defined by an inner surface 102 of the airway 100. The illustrated inner surface 102 is defined by a folded layer of epithelium 110 surrounded by stroma 112a. A layer of smooth muscle tissue 114 surrounds the stroma 112a. A layer of stroma 112b is between the muscle tissue 114 and connective tissue 124. Mucous glands 116, blood vessels 120, and nerve fibers 122 are within the stroma layer 112b. Smooth muscle bands 114a extend longitudinally along the posterior side of the airway 100, which is relatively loose when compared to the other portions of the airway 100 that are supported by the cartilage rings 28. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 and mucous glands 116 via the nerve fibers 122. Additionally, signals are transmitted from sensory receptors (e.g., cough, irritant, and stretch) through the nerve trunks 45 to the central nervous system.

Figure 5:
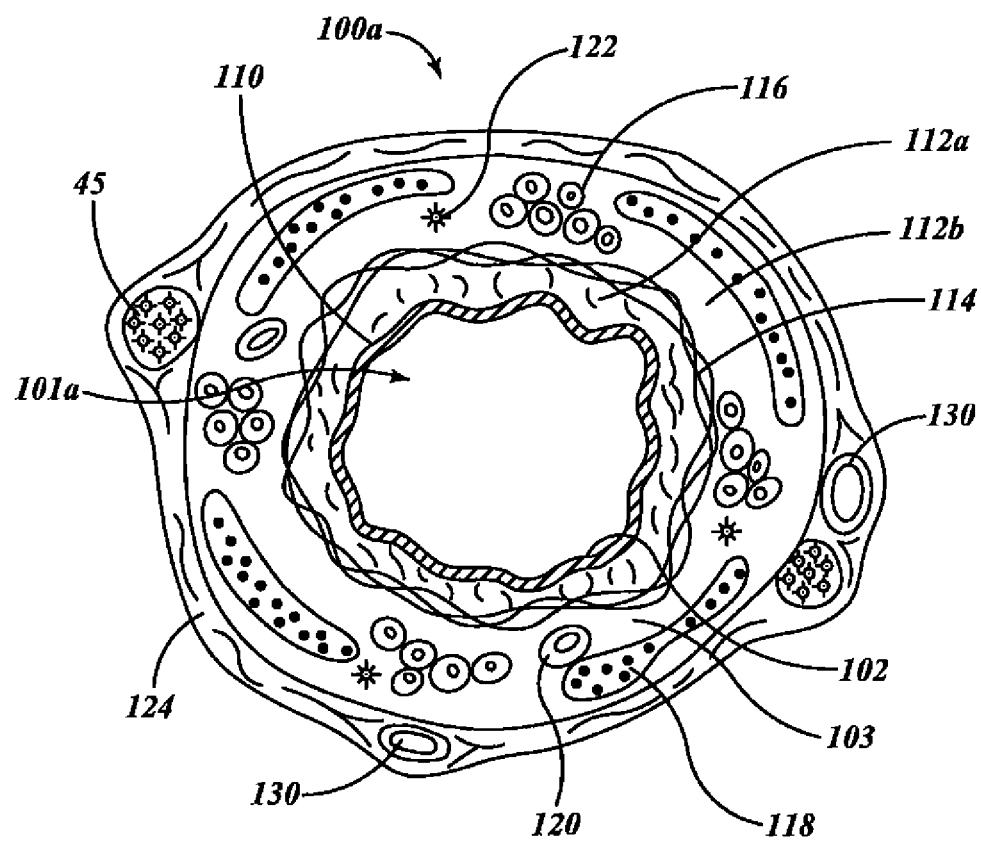
Figure 6:
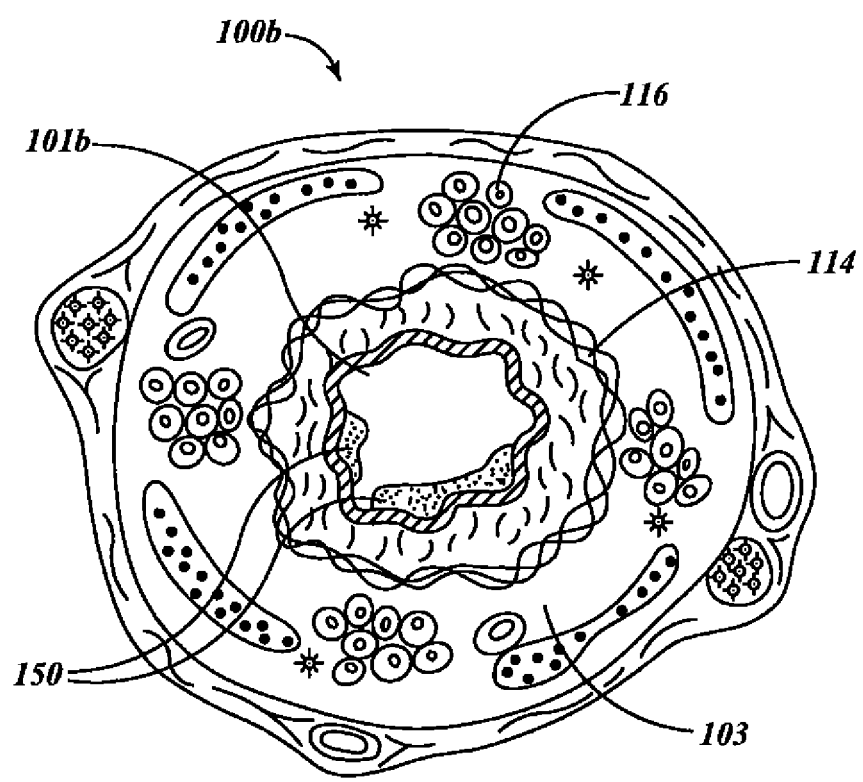

FIGS. 5 and 6 illustrate cross-sectional views of higher generation airways in healthy and diseases lungs, respectively. For the purpose of this disclosure, airway branches are numbered in generations starting down from the main stem at generation 0, continuing to the main bronchi at generation 1, and on to the more distal branches at generation 2 and higher. FIG. 5 is a cross-sectional view of a distal airway 100a of the bronchial tree 27 in a healthy lung. FIG. 6 is a cross-sectional view of a distal airway 100b that is affected by a pulmonary disease. The representation in FIGS. 5 and 6 is a generalized view that is intended to be representative of airways distal of the dashed lines 27a and 27b in FIG. 2. The example airways 100a and 100b include cartilage plates 118 rather than cartilage rings 28.

The lumen 101b of the airway 100b in FIG. 6 is significantly narrower than the lumen 101a of the healthy airway 100a, and is partially blocked by excess mucus 150. Depending on the patient, the reduced size of the lumen 101b can be attributable to variety of ailments, including, for example, inflammation of the airway wall 103, constriction of the smooth muscle tissue 114, or excessive intraluminal mucus or edema fluid, or both.

Figure 7:
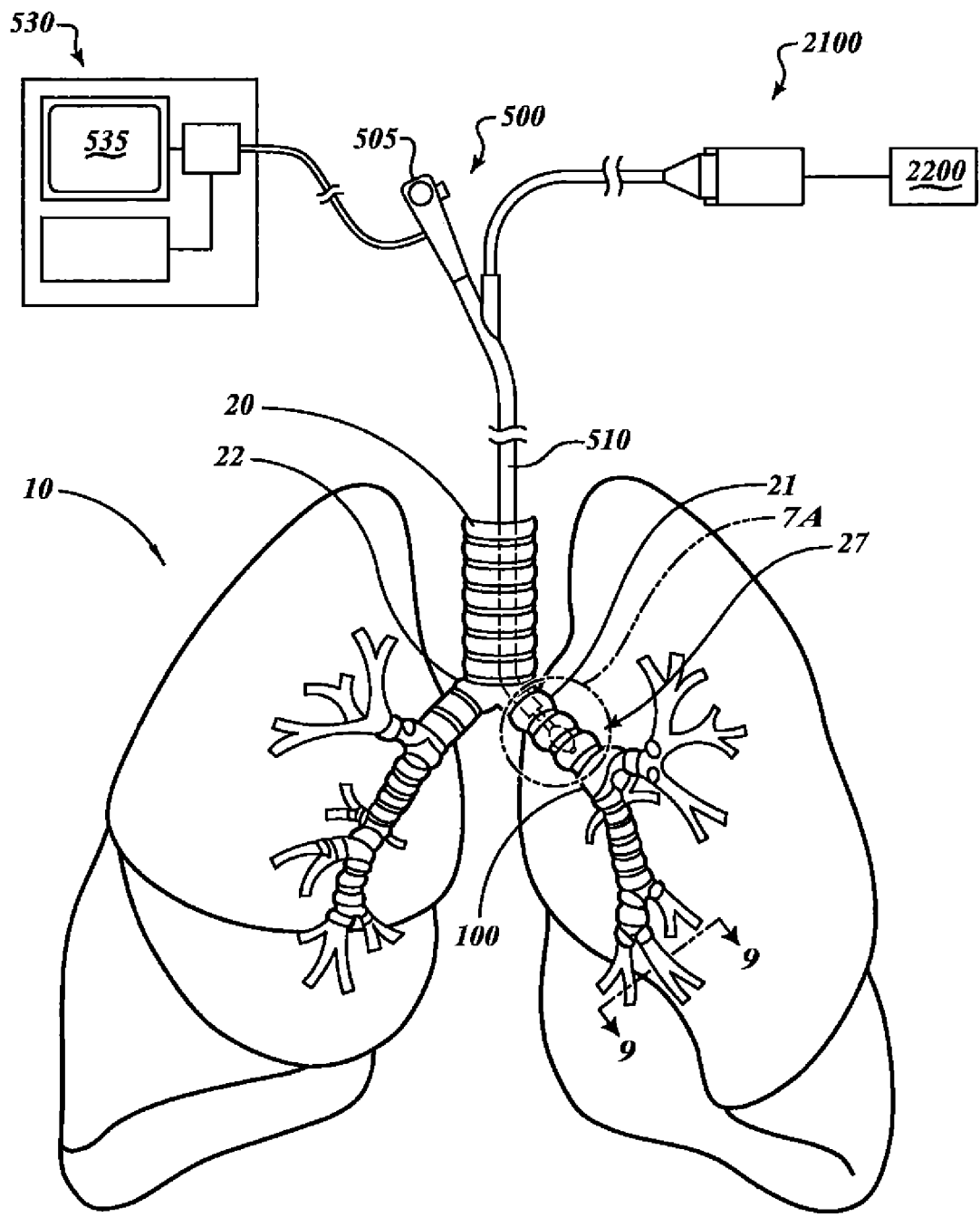

FIGS. 7 and 8 provide an overview of one example method and system that can be used to treat diseased airways such as the one shown in FIG. 6. It has been found that attenuating the transmission of signals traveling along the vagus nerves 41, 42 can alter airway smooth muscle tone, airway mucus production, airway inflammation, and the like in airways distal to the treatment site. Attenuation can include, without limitation, hindering, limiting, blocking, and/or interrupting the transmission of signals. For example, the attenuation can include decreasing signal amplitude of nerve signals or weakening the transmission of nerve signals.

Figure 7A:
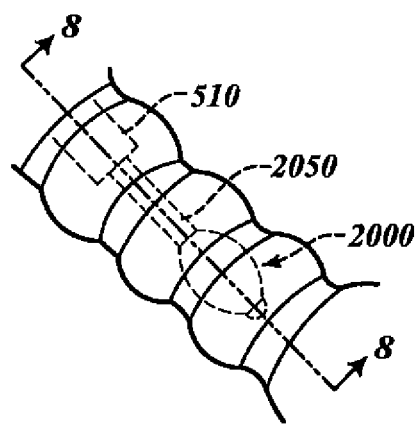

FIGS. 7 and 7A illustrate the agent delivery system 2000 positioned within the left main bronchus 21 of a patient for a treatment session. In this example, the agent delivery system 2000 is advanced to the treatment site via a working channel of a flexible bronchoscope 500. In this regard, it can be said that the agent delivery system 2000 shown in FIG. 7A is compatible with the working channel of the flexible bronchoscope 500. Utilizing the working channel of a flexible bronchoscope to position an agent delivery system in a patient's airway has numerous benefits, including obviating the need to separately navigate the bronchoscope and the agent delivery system to the treatment site, providing a repeatable delivery location for the agent delivery system, and improving visualization of the delivery and treatment.

Further, although the agent delivery systems described herein advantageously allow for a compact profile that facilitates compatibility with the working channel of a flexible bronchoscope, the aspects described herein are not so limited. For example, as will be readily apparent to one of ordinary skill in the art upon a complete review of the present disclosure, the aspects disclosed herein are also scalable to be compatible with larger working lumens that may or may not be associated with a bronchoscope. Notably, the present disclosure is not limited solely to systems that are delivered via the working channel of a bronchoscope, but also encompasses systems delivered by other means, such as an independent sheath and/or delivery catheter.

FIG. 7 further illustrates an insertion tube 510 of the bronchoscope extending from a control section 505 external to the patient body, through the trachea 20, and to a treatment site within the left main bronchus 21. The bronchoscope 500 can be coupled to a video system 530, which allows a practitioner to observe progress of the insertion tube 510 through the patient on a monitor 535 as the insertion tube 510 is steered with the assistance of the control section 505. Although the agent delivery system 2000 is positioned in the left main bronchi in this example, the agent delivery system 2000 can be positioned in other locations outside the lung, such as within the right main bronchi, the lobar bronchi, and bronchus intermedius. The bronchus intermedius is the portion of the right main bronchus between the upper lobar bronchus and the origin of the middle and lower lobar bronchi. The agent delivery system 2000 can also be positioned in higher generation airways (e.g., airway generations>2) to affect remote distal portions of the bronchial tree 27. The agent delivery system 2000 can be navigated through tortuous airways to perform a wide range of different procedures, such as, for example, to deliver an agent to affect nerve activity in a portion of a lobe, an entire lobe, multiple lobes, or one lung or both lungs. In some embodiments, the lobar bronchi are treated to affect nerve activity in lung lobes. For example, one or more treatment sites along a lobar bronchus may be targeted to affect nerve activity in an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

In this example, the agent delivery system 2000 is coupled to a steering mechanism 2100 and a fluid supply portion 2200.

In the present example, the agent delivery system 2000 delivers one or more treatment agents to an airway wall at a treatment site to affect activity of the nerves 122 or the nerve trunks 45 at the treatment site. As noted above, it has been found that attenuating the transmission of nervous system signals can alter airway smooth muscle tone, airway mucus production, airway inflammation, and the like in airways distal to the treatment site. Attenuation can include, without limitation, hindering, limiting, blocking, and/or interrupting the transmission of signals. For example, the attenuation can include decreasing signal amplitude of nerve signals or weakening the transmission of nerve signals.

In the present example, an agent is delivered to an airway wall to attenuate nervous system signals of nerves 45 that extend along the airway wall 100. For example, an agent can affect nerves at least about 1 mm radially outward from an inner surface of the airway wall. In some examples, the agent affects nerves as deep as 8 mm radially outward from an inner surface of the airway wall. In some examples, the agent affects nerve trunks extending along an outer surface of the airway wall.

Exemplary non-limiting treatment agents include, without limitation, one or more antibiotics, anti-inflammatory agents, pharmaceutically active substances, bronchoconstrictors, bronchodilators (e.g., beta-adrenergic agonists, anticholinergics, etc.), nerve blocking drugs, photoreactive agents, neurotoxins such as botulinum toxin, serotype A or botulinum toxin, serotype B including or combinations thereof. For example, long acting or short acting nerve blocking drugs (e.g., anticholinergics) can be delivered to nerve tissue extending along an airway wall to temporarily or permanently attenuate signal transmission. Substances can also be delivered directly to the nerves 122 or the nerve trunks 45, or both, to chemically damage the nerve tissue.

Other examples of agents that can induce axonal degeneration include calcium ionophores. An ionophore is a lipid soluble molecule usually synthesized by microorganisms to transport ions across the lipid bilayer. Calcium specific ionophores artificially increase intracellular calcium in axons. Increased intracellular calcium induces axonal degeneration through a mechanism similar to what occurs after axotomy.

In another example, the agent can include molecules that deplete intracellular Nmnat (nicotinamide mononucleotide adenyltransferase). Nmnat are enzymes that catalyze the chemical reaction that changes ATP to NAD. Nmnats are essential survival factors for maintenance of healthy axons. Depletion of isoforms of these enzymes in axons induces degeneration that is consistent with the degeneration that occurs after axotomy.

In another example, an agent can be rotenone and any molecule that cause mitochondrial dysfunction. These agents work by interfering with the electron transport chain in mitochondria. Rotenone works by inhibiting transfer of electrons from iron sulfur centers in complex 1 to ubiquinone. This interferes with NADH during the ATP synthesis.

Other examples of agents can include chemotherapy agents. For example, platinum agents (cisplatin, carboplatin, oxaliplatin), *Vinca* alkaloids (vinscristine, viniblastine), Taxanes (paclitaxel, docetaxel), Epothilones (ixabepalone), bortezomib, thalidomide, and lenolidamide.

There are three broad categories within which agents applied to an airway may act on nerves to disrupt nerve signaling. In the first category, an agent applied to an airway wall comes into contact with the nerve axons, is retrogradely transported to the cell body, and is toxic to the cell body thereby killing the cell body and all axons derived from that cell body, a process known as suicide transport. The broad class of agents that can cause this category of disruption are ribosome-inactivating proteins (RIPs). Specific agents include, but are not limited to ricin, abrin, and saporin. Ricin, for example, has been studied extensively for delivery to peripheral nerves, causing retrograde somal ablation with 50 ng to 3 μg doses. These types of agents have the potential to cause long term effects on nerve transmission.

In a second category, an agent applied to an airway causes injury to a nerve axon at the site of contact with loss of axons distal to the treatment site. However, axons proximal to the treatment site and the cell body, itself, remain intact. Agents that can cause this category of disruption include those that cause general injury to cells at a treatment site, such as phenol (3%), ropivacaine (also referred to as rINN, a local anesthetic that been shown to ablate nerve axons), sodium tetradecyl sulfate (STS) (1%-3%), polidocanol, ethanol (99.5%), sugar (hypertonic [50%] dextrose solution), ethanolamine oleate (5%), and sodium morrhuate (5%). Other agents that can cause this category of disruption include those that can cause neuronal specific injury, such as arsenic, nitric oxide, and glutonate.

In a third category, an agent that is supplied to an airway interferes with and/or prevents nerve signal conduction past the treatment site. Some agents that can cause short term disruption include, but are not limited to, lidocain, bupivacaine, mepivacaine, procainamide, mexiletine, tocainide. Other agents that can cause longer term disruption include, but are not limited to, tetrodotoxin (blocking effects on the $Na^+$ ion channel), tetraethylammonium (blocking effects on $K^+$ ion channels), chlorotoxin (blocking effects on $Cl^-$ ion channels).

Figure 8A:
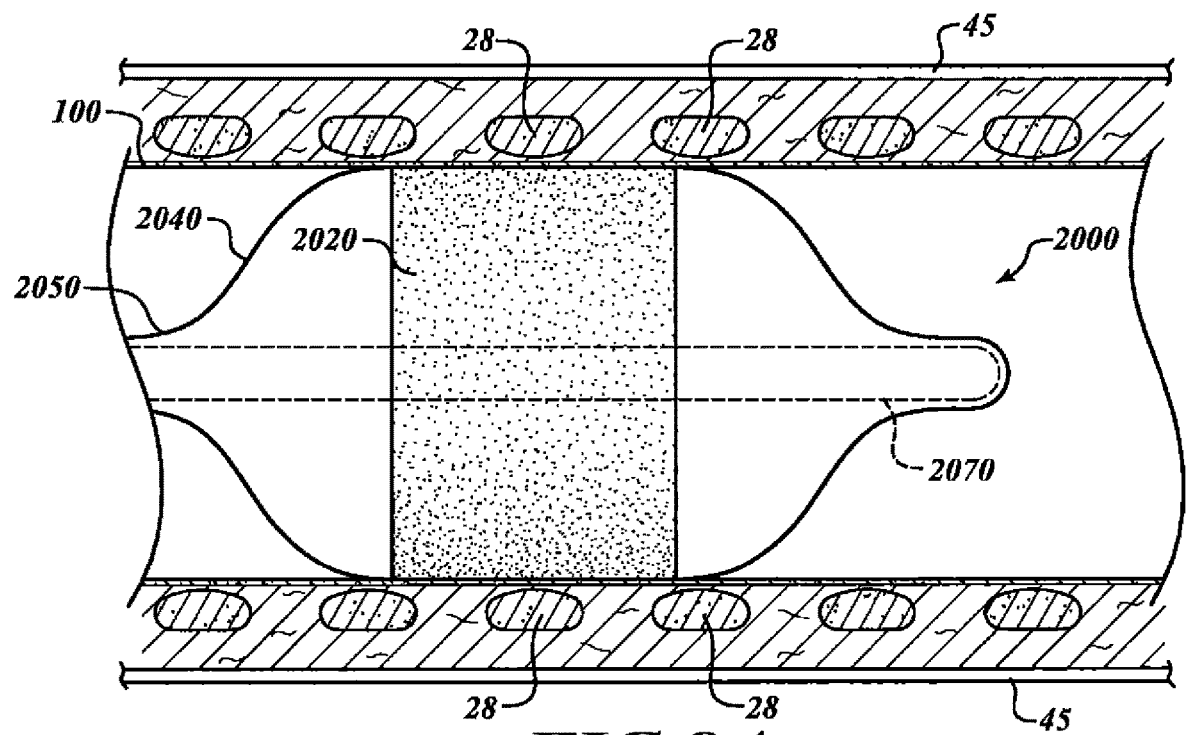
Figure 8B:
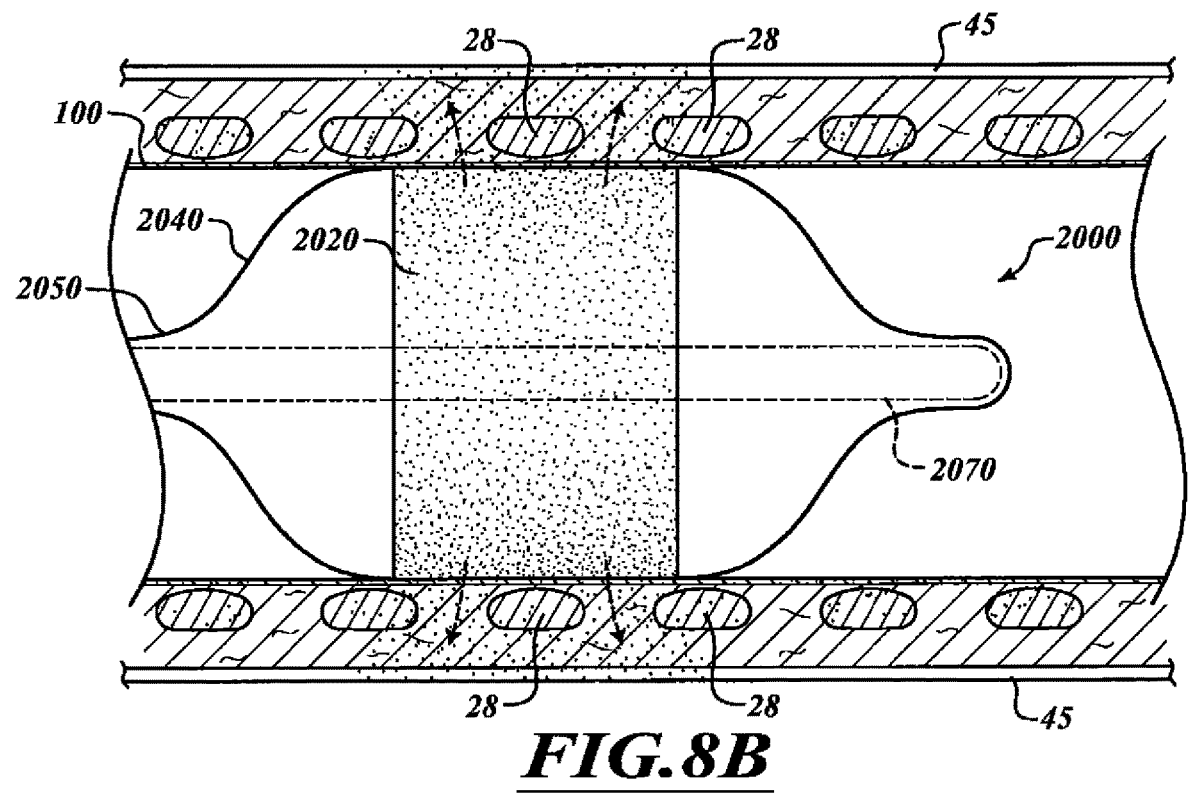

FIGS. 8A and 8B are side elevation views, taken along line 8-8 of FIG. 7A, of the agent delivery system 2000 in the left main stem bronchus 21. FIG. 8A is a longitudinal side view of a treatment system 2000 in the form of a balloon expandable, agent delivery catheter. The illustrated agent delivery system 2000 is in an expanded state. The expanded agent delivery system 2000 includes an expandable member 2040 and an agent delivery portion 2020. The agent delivery portion 2020 can be collapsed inwardly when the agent delivery system 2000 is moved (e.g., pulled proximally or pushed distally) through a delivery assembly, such as, for example, the working channel of the bronchoscope 500. When the agent delivery system 2000 is pushed out of the delivery assembly, the agent delivery portion 2020 can be expanded outward by inflating the expandable member 2040. As discussed in greater detail below, the agent delivery portion 2020 can be a coating directly applied to the expandable member 2040 or a coating on a strip of material coupled to the expandable member 2040.

The agent delivery system 2000 generally includes the expandable member 2040 (illustrated in the form of a distensible balloon), an agent delivery portion 2020, a support element 2070, and an elongate member 2050.

An interior of the expandable member can be in fluid communication with the fluid supply 2200 via a lumen that extends through the elongate member 2050. The fluid can include, without limitation, a gas, a temperature controlled fluid, such as water, saline, or other fluid suitable for use in a patient.

Different types of materials can be used to form different components of the agent delivery system 2000. In some embodiments, the expandable member 2040 is made, in whole or in part, of a distensible, chemically inert, non-toxic, electrically insulating, and thermally conductive material. For example, the expandable member 2040 may be made of polymers, plastics, silicon, rubber, polyethylene, nylon, polyethylene terephthalate (PET), combinations thereof, or the like. The expandable member can have, for example, a barrel length in the range of from about 5 mm to about 35 mm. The diameter of the deflated expandable member 2040 can be relatively small. For example, a maximum diameter of the expandable member 2040 can be in a range of about 1 mm to about 3 mm when the expandable member 2040 is fully collapsed. To treat a bronchial tree of a human, the diameter of the expandable member 2040 can be in a range of about 6 mm to about 20 mm. For enhanced treatment flexibility, the inflated expandable member 2040 diameter may be in a range of about 7 mm to about 25 mm. Of course, the expandable member 2040 can be other sizes to treat other organs or tissue of other animals.

The longitudinally extending, axial support 2070 is, in this example, a centrally located axial shaft. The axial support can include a shape memory material and/or stainless steel. Shape memory materials include, for example, shape memory metals or alloys (e.g., Nitinol), shape memory polymers, ferromagnetic materials, combinations thereof, and the like. The axial support can aid in pushability of the expandable member 2040 while allowing the expandable member 2040 to be formed of a lightweight, highly compliant material. For example, the axial support 2070 can function as a push rod to advance the expandable member 2040 in its flimsy, deflated state through the working conduit of the flexible bronchoscope 500 to a treatment site in an airway of the patient.

In some embodiments, the elongate member 2050 is made, in whole or in part, of any suitable flexible, chemically inert, non-toxic material for withstanding operating pressures without significant expansion. The elongate member 2050 can have a suitable length to be passed into the lung and bronchial tree.

The overall working length of the agent delivery system 2000 can range from 300 to 1000 millimeters in length, depending on the location of the bronchial tree where treatment is to be performed and, in some instances, the working length of the working channel of the flexible bronchoscope. Flexible bronchoscopes typically include a working length of 600 mm, but can range in length from 300 mm to 1000 mm. The agent delivery system 2000 can have a working length suitable for treatment of airways up to and including the main stem bronchi, or a working length for treatment of airways up to the and including the lobar bronchi. Working lengths up to 1000 mm are also within the scope of the present disclosure for treatment of airways distal the lobar bronchi. In one example, an agent delivery system 2000 with a working length of about 760 millimeters facilitates access to and treatment of the main stem bronchus. The agent delivery system 2000 can be flexible enough to accommodate a working channel with a bending radius of 3.1 mm or less, or, in some examples, 2.7 mm or less. Further the agent delivery system 2000, in a collapsed delivery state, can be advanced through a working channel having a diameter in the range of about 1.0 millimeters to about 6.0 millimeters, in one example. In other examples, the agent delivery system 2000, in a collapsed delivery state, can be advanced through a working channel having a diameter in the range of about 1.0 millimeters to about 4.0 millimeters. In other examples, the agent delivery system 2000, in a collapsed delivery state, can be advanced through a working channel having a diameter in the range of about 1.2 millimeters to about 3.2 millimeters. Other lengths are also possible.

The shapes and structure of the agent delivery portion 2020 and the expandable member 2040 can be selected such that the agent delivery portion 2020 and expandable member 2040 expand/deflate together. When the expandable member 2040 is inflated, the agent delivery portion 2020 is expanded with the expandable member 2040. When the expandable member 2040 is deflated, the agent delivery portion 2020 contracts with the expandable member 2040. The agent delivery portion 2020 may include a drug or other agent dried on an exterior surface of the expandable member 2040. The agent delivery portion 2020 can further include excipients such iopromid, urea, shellac and butyryl-trihexyl citrate (BTHC), that modulate between short term and long term release of the agent. In another example, the agent can be entrapped in a microsphere on the agent delivery portion that would open when the agent delivery portion 2020 engages an airway wall.

In another example, the agent delivery portion 2020 can include a strip of material that is coated with the agent and then coupled to the expandable member 2040. The strip of material can be formed of any material that is compatible with the expandable member, such as, for example, polytetrafluoroethylene (PTFE), nylon, polyethylene terephthalate (PET), and/or urethane.

In the present example, the agent delivery portion 2020 extends around an entire circumference of the expandable member 2040 and has a length ranging from 1.0 to 5.0 cm and width ranging from 0.1 mm to 25 mm. However, other sizes and shapes are within the scope of the present disclosure. Further, though preferable, it is not required that the agent delivery portion 2020 extend around the entire circumference of the expandable member 2040. In other example, the agent delivery portion 2020 extends around, for example an arc of 90, 180, or 270 degrees around the expandable member 2040. In other examples, the agent delivery portion 2020 can include of segments that form a non-continuous band around the expandable member 2040. In other examples, multiple, axially offset strips or segments could be used. Each strip could be sized to fit between adjacent cartilage rings. Such strips could range in width from 0.1 to 4.0 mm.

The balloon expandable agent delivery portion 2020 can be delivered into the airways of the lung with the expandable member 2040 deflated and the agent delivery portion 2020 contracted. The agent delivery portion 2020 and expandable member 2040 can be kept in a collapsed or closed configuration to allow the agent delivery system 2000 to pass easily through the lungs. The agent delivery system 2000 is moved through the airways until the agent delivery portion 2020 is at the desired treatment location. Once in position, fluid is allowed to flow through the elongate member 2050 and into the expandable member 2040 using any conventional valve and/or fluid control mechanism that would be readily apparent to one of ordinary skill of art upon a review of the entirety of the present disclosure. The fluid inflates the expandable member 2040 which in turn expands the agent delivery portion 2020. Flow of the fluid either into or out of the expandable member 2040 can be regulated such that the expandable member 2040 continues to inflate until the agent delivery portion 2020 is brought into contact with or proximate to the airway wall 100, as shown in FIGS. 8A and 8B.

As shown in FIG. 8B, after the agent delivery portion 2020 is brought into contact with the airway wall 100, the agent can detach from the agent delivery portion 2020 and migrate through the airway wall 100 to affect the nerve trunks 45 that run along the airway wall 100. The amount of dwell time required can depend on the excipient chosen as well as the technique of application. For example, transfer of the agent to the airway wall can be facilitated through rotating the expandable member 2040 while it is in contact with the airway wall 100. In general, the dwell time for an agent coated balloon can range from 30 seconds to 30 minutes.

Figure 9A:
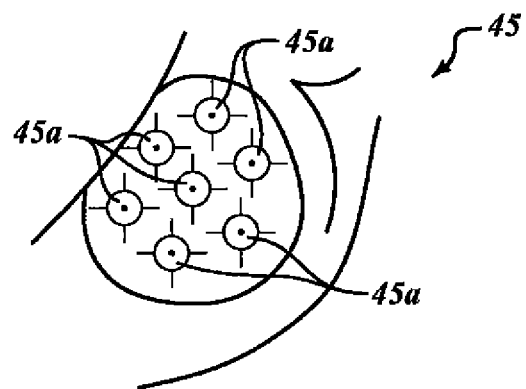
Figure 10A:
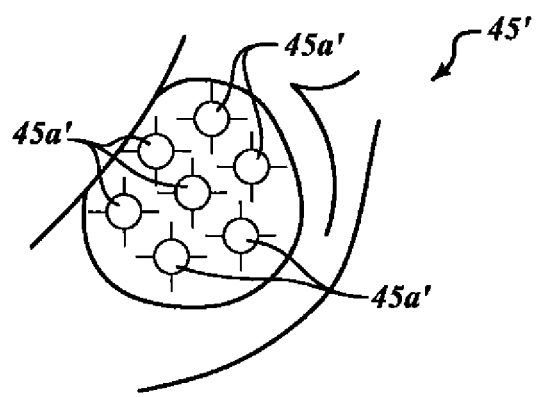

The effects of the example treatment described above on distal airways will now be discussed with reference to FIGS. 9 and 10. FIG. 9 is a cross-sectional view of a distal airway in the lung, taken along line 9-9 of FIG. 7, prior to treatment. FIG. 10 is a cross-sectional view of the same airway after treatment. FIGS. 9A and 10A provide detailed views of nerve axons of a nerve trunk associated with the distal airway before and after the treatment, respectively.

As shown in FIG. 9, prior to treatment, the lumen 101$b$ of the airway 100$b$ narrow and is partially blocked by excess mucus 150. Depending on the patient, the reduced size of the lumen 101$b$ can be attributable to variety of ailments, including, for example, inflammation of the airway wall 103, constriction of the smooth muscle tissue 114, or excessive intraluminal mucus or edema fluid, or both.

Following treatment, as shown in FIG. 10, the lung lumen 101$c$ has opened a significant amount, and mucus production is greatly reduced. In some instances, the increase in lumen size and/or decrease in mucus production can be attributable to nerve death at the treatment location due to, for example, poising from the agent, and the resulting nerve death at more distal portions of the affected nerve. Using agents that cause either the first or second category of disruption discussed above can result in loss of nerve axons distal of the treatment. For these types of treatments, it may be the case that the nerve axons that are present in the distal airways, as shown in FIG. 9A, are no longer present, as shown in FIG. 10A. Nevertheless, the function of other tissue or anatomical features, such as the mucous glands, cilia, smooth muscle, body vessels (e.g., blood vessels), and the like can be maintained even though the nerve tissue is injured. In other examples, such as the third category of nerve disruption discussed above, the agent interrupts nerve activity at the treatment location without causing nerve death at distal locations. In this case, the beneficial effects illustrated in FIG. 10 may result without the loss of nerve axons as shown in FIG. 10A.

As a result of the treatment, the nerve supply along a section of the bronchial tree can be cut off. When the signals are cut off, the distal airway smooth muscle can relax, which can lead to the airway dilation seen in FIG. 10. Cutting the nervous system signals can also causing mucous cells to decrease mucous production leading to the reduced amount of mucous in the lumen 101$c$ of FIG. 10. The treatment may also cause inflammatory cells to stop producing airway wall swelling and edema. For example, the occurrence of acetylcholine receptors may be increased, while inflammatory cells, inflammatory cytokines, and other markers in the distal airway may be reduced.

All of these changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

In addition to the near-term benefits, interrupting nervous system signal communication with distal airways has the long term effect of remodeling previously constricted airways beyond simply relaxing the smooth muscle tissue or reducing mucous production. For example, without nervous signals causing them to contract, the smooth muscle will begin to atrophy over time. Eventually, smooth muscle and muscle gland mass will decrease. In addition, there will be a decrease in airway wall fluid, such as edema and interstitial tissue fluid. As such, unlike temporary treatments that block nervous system signals for discrete periods of time, it is expected that the amount of obstruction in distal airways will continue to decrease over time following a treatment with the agent delivery systems of the present disclosure.

Figure 11:
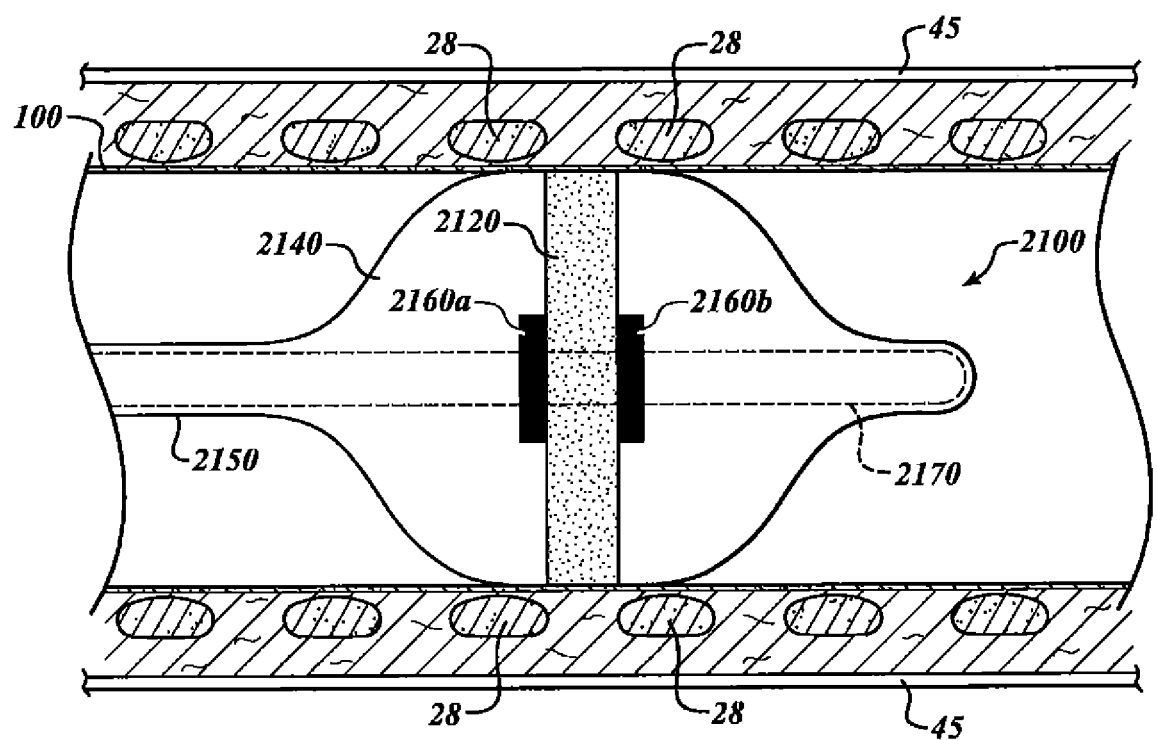
Figure 12:
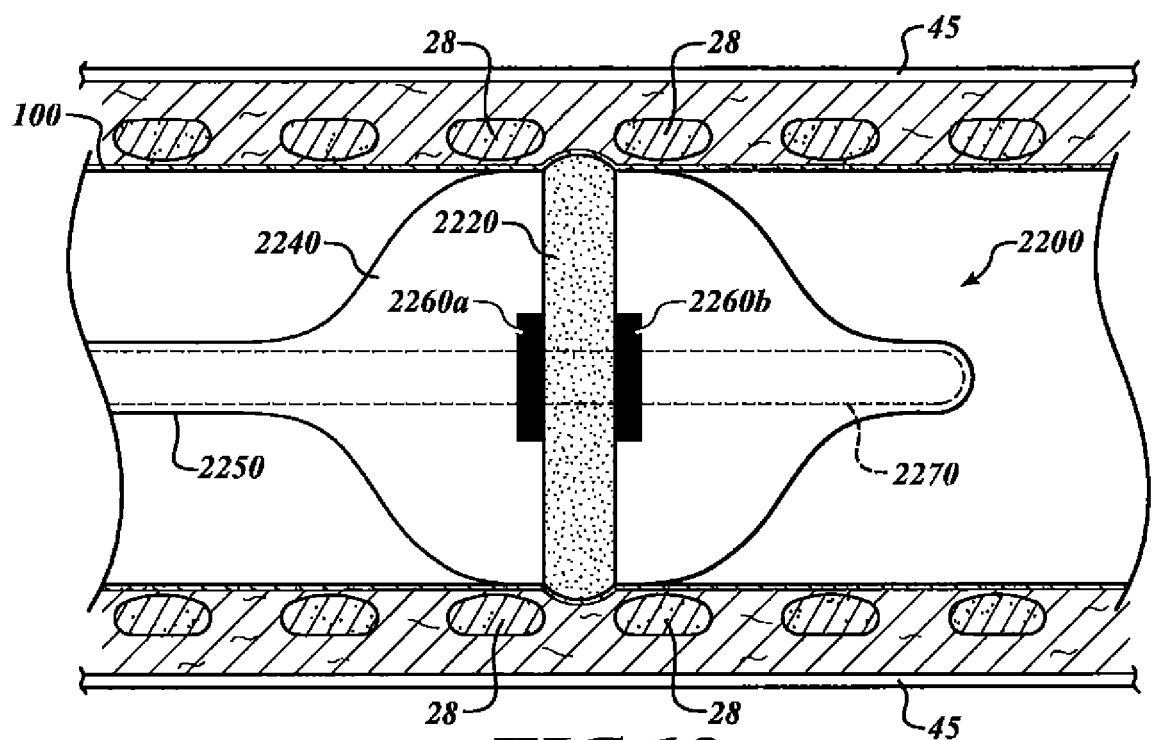
Figure 13:
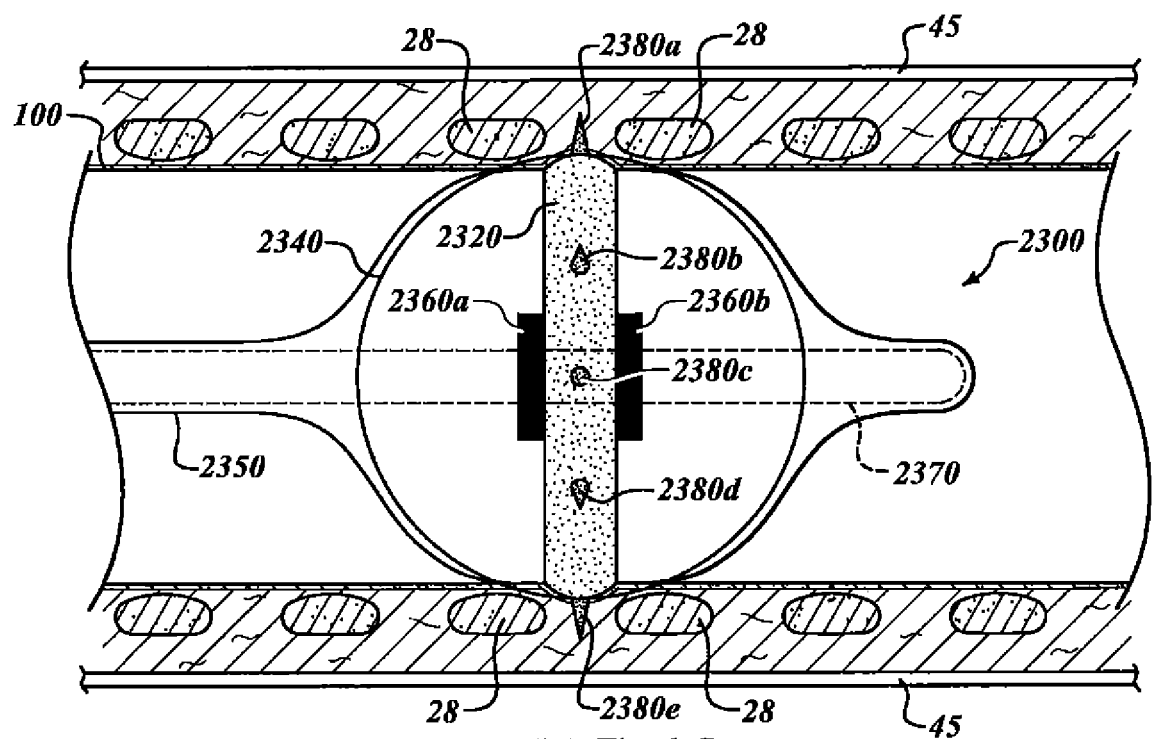
Figure 14:
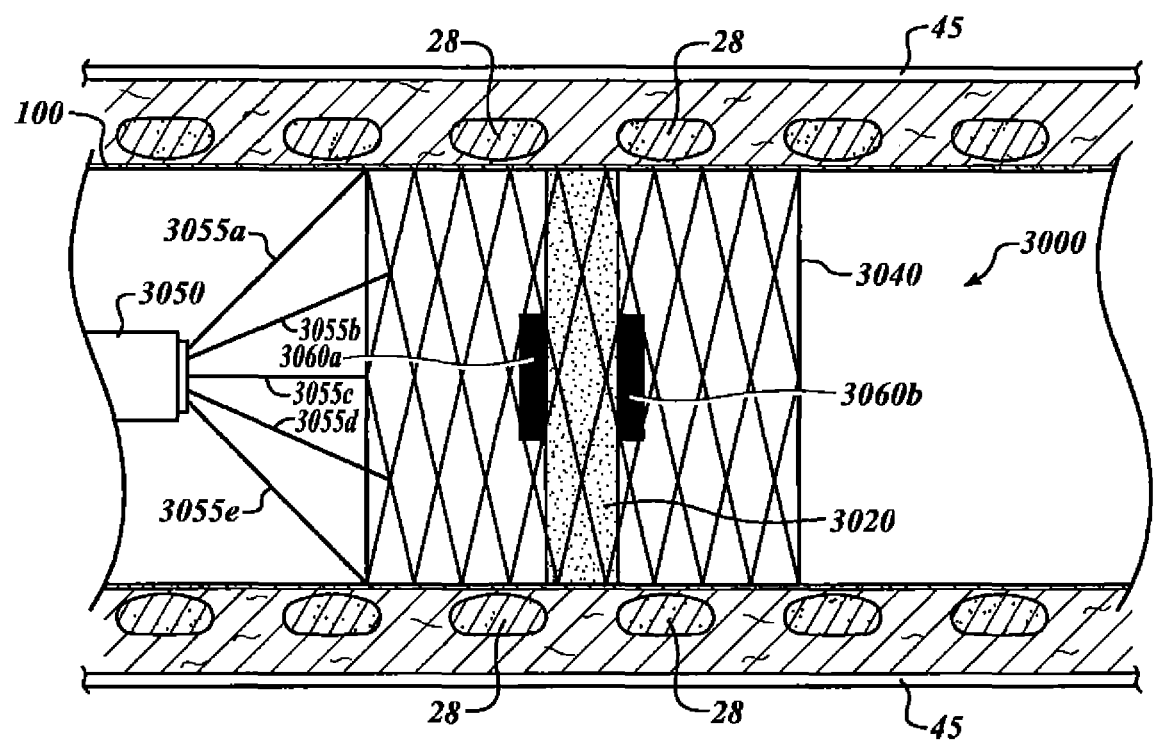

FIG. 11 illustrates an agent delivery system 2100 that includes features that facilitate positioning the agent delivery portion and, in some cases, applying a treatment in a space between adjacent cartilage rings. The agent delivery system 2100 generally includes the expandable member 2140 (illustrated in the form of a distensible balloon), an agent delivery portion 2120, a support element 2170, an elongate member 2150, and marking elements 2160$a$ and 2160$b$.

The agent delivery system 2100 is generally similar to the agent delivery system 2000 described above, with the exception of the inclusion of the marking elements 2160$a$ and 2160$b$ on either side of the agent delivery portion 2120. The marking elements could be, for example, radiopaque markers made of, for example, tungsten or platinum. The markers could be inks, films, or coatings that can be made of metal, conductive polymers, or other suitable materials formed by a deposition process (e.g., a metal, such as gold, tungsten, or platinum, deposition process), coating process, etc., and can comprise, in whole or in part, silver ink, silver or gold epoxy, combinations thereof, or the like.

Although shown as single elements arranged on opposite sides of the agent delivery portion 2120, a single marking element could be arranged on one side of the agent delivery portion 2120. In other examples, the marking elements can be arrayed circumferentially around the expandable member 2140 to facilitate visualization of the agent delivery portion 2120 on multiple sides.

As with the agent delivery system 2000 described above, the width of the agent delivery portion 2120 can be specifically tailored to fit entirely between two adjacent cartilage rings 28. In this example, the width of the agent delivery portion 2120 can be in a range of between about 0.1 mm and about 4.0 mm. Further, multiple axially offset strips and/or segments could include marking elements to facilitate placement between cartilage rings of the airway.

Visualization could be achieved by optically coupling an optical element of a bronchoscope to a portion of the expandable member 2140 to directly visualize the marking elements 2160*a* and 2160*b*, coating 2120, and/or the airway wall. Optical coupling is discussed in U.S. Provisional Patent Application No. 61/786,203, filed on Mar. 14, 2013, and U.S. patent application Ser. No. 13/894,920, filed on May 15, 2013, both of which are titled "Compact Delivery Pulmonary Treatment Systems and Methods for Improving Pulmonary Function," the entire contents of each are incorporated herein by reference.

FIG. 12 illustrates an agent delivery system 2200 that includes features that further facilitate positioning the agent delivery portion and, in some cases, applying a treatment in a space between adjacent cartilage rings. The agent delivery system 2200 generally includes the expandable member 2240 (illustrated in the form of a distensible balloon), a raised agent delivery portion 2220, a support element 2270, an elongate member 2250, and marking elements 2260*a* and 2260*b*.

The agent delivery system 2200 is generally similar to the agent delivery system 2200 described above, with the exception that the agent delivery portion 2220 generally protrudes beyond a surface of adjacent surfaces of the expandable member 2240 to act as a positioner. The raised agent delivery portion 2220 is, in some examples, a band that stays in place due to friction between the band and the expandable member 2240. Such a raised delivery portion 2220 can be expandable together with the expandable member 2240. In other examples, the raised delivery portion 2220 can be a ring that is tethered to the expandable member 2240. Such a tether could include several sutures to a thin film that extends at least partially around a circumference of the expandable member 2240 to anchor the expandable member 2240. The thin film can extend entirely around the circumference of the expandable member. In yet another example, the raised delivery portion is a ring tethered to the expandable member 2240. In yet another example, the raised delivery portion is molded from the expandable member itself such that it is integral with the sidewall of the expandable member.

Positioners can facilitate positioning of the agent delivery portion 2220. Such positioners include, without limitation, bumps, bulges, protrusions, ribs or other features that help preferentially seat the agent delivery portion 2220 at a desired location, thus making it easy to administer the agent or to verify correct positioning.

The agent delivery portion 2220 can be a ring that is movable relative to the expandable member 2240. The agent delivery portion 2220 can serve as an intercartilaginous positioner. When the expandable member 2240 presses against the airway 100, the ring moves along the expandable member 2240 to preferentially position ring between cartilage rings 28, 28. The ring forming the agent delivery portion 2220 protrudes outwardly from the expandable member 2240 a sufficient distance to ensure that the agent delivery portion 2220 applies sufficient pressure to the airway wall to cause self-seating. The agent delivery system 2200 can be moved back and forth to help position the agent delivery portion 2220 next to soft compliant tissue in the space between the adjacent rings 28, 28.

The marking elements 2260*a* and 2260*b* can be coupled to either the expandable member 2240, the agent delivery system 2200, or both.

FIG. 13 illustrates an agent delivery system 2300 that includes features that further facilitate delivery of the agent to the nerve trunks 45 that extend along the airway 100. The agent delivery system 2300 generally includes the expandable member 2340 (illustrated in the form of a distensible balloon), a raised agent delivery portion 2320, a support element 2370, an elongate member 2350, marking elements 2360*a* and 2360*b*, and needles 2380*a*, 2380*b*, 2380*c*, 2380*c*, 2380*d*, 2380*e* (collectively, the needles 2380).

The agent delivery system 2300 is generally similar to the agent delivery system 2200 described above, with the exception of the inclusion of the needles 2380 that project from the surface of the agent delivery portion 2320. The needles 2380 can be fully coated and be arrayed to extend around a full circumference of the expandable member 2340. In other examples, the needles can extend around only a portion of the expandable member 2340 to allow a practitioner to target nerves that are located primarily posteriorly.

The needles can extend from, for example, 0.5 mm to 5 mm from a surface of the delivery portion 2320. As the expandable member 2340 is inflated, the needles 2380 can penetrate the airway wall to deliver the agent to an area proximate the nerve trunks 45. As with the previous embodiments, positioning and placement can be facilitated by optically coupling the expandable member 2340 to, for example, a bronchoscope. The combination of long needles and positioning elements can be particularly beneficial for avoiding cartilage rings while also effectively delivering an agent to a nerve trunk 45.

FIG. 14 illustrates an embodiment in which the expandable member takes the form of an expandable and collapsible basket rather than balloon. The agent delivery system 3000 generally includes the expandable member 3040 (illustrated in the form of an expandable and collapsible basket), an agent delivery portion 3220, a plurality of movable arms 3055*a*, 3055*b*, 3055*c*, 3055*c*, 3055*d*, and 3055*e* (collectively arms 3055), an elongate member 3250, and marking elements 3260*a* and 3260*b*.

In this example, the expandable member 3040 is a basket that can be deployed from a lumen in the elongate element 3050. The movable arms can facilitate moving the basket 3040 from a collapsed delivery state to an expanded, delivery state. The arms 3055 and the basket 3040, which may be a conductive shape memory material such as Nitinol, can be resiliently biased outwardly such that when extended distally from elongate element 3050, they return to a radially expanded configuration as shown in FIG. 14, and thereby urge the basket 3040 against the airway wall.

Advantageously, the open framework structure of the basket 3040 allows a patient to breath during treatment, as the agent detaches from the agent delivery portion 3220. The agent delivery portion 3220 can include, in this example, excipients such as polylactide (PLA), its copolymers with glycolide (PLGA), iopromid, urea, shellac and butyryl-trihexyl citrate (BTHC), or non-biodegradable substances such as fluoropolymer or styrene-isobutylene-styrene, or any combination thereof. The basket 3040 could be coated along the open framework that makes up the struts to form the agent delivery portion 3220. In another example, as depicted in FIG. 14, the agent delivery portion 3220 is on a strip of material can be formed of any material that is compatible with the expandable member, such as, for example, polytetrafluoroethylene (PTFE) or urethane, that covers the basket 3040. The strip of material could be fully or partially covered with the agent. As with the previous examples, the agent delivery portion 3220 delivery portion can be sized for positioning between adjacent cartilage rings. Likewise, several axially offset strips or segments of delivery portion 3220 delivery portion could be used.

In this example, the marking elements 3260*a* and 3260*b* could be placed on the basket 3040 to aid in identification of the coated portion of the basket 3040 and aid in aligning the agent delivery portion 3220 between adjacent cartilage rings.

Figure 15:
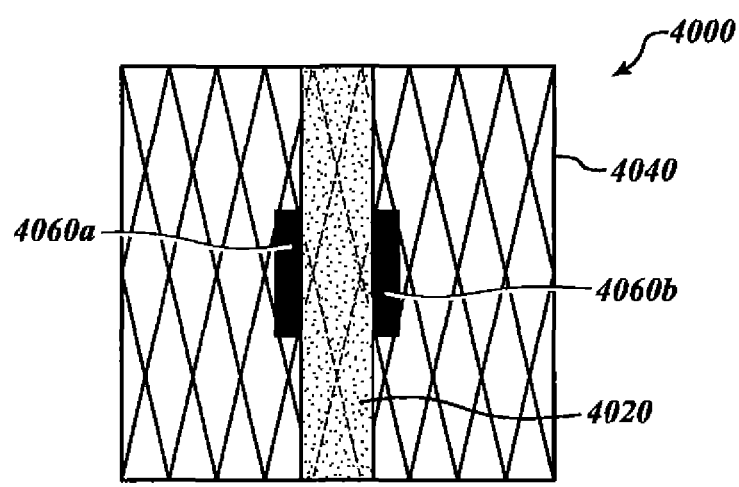
Figure 16:
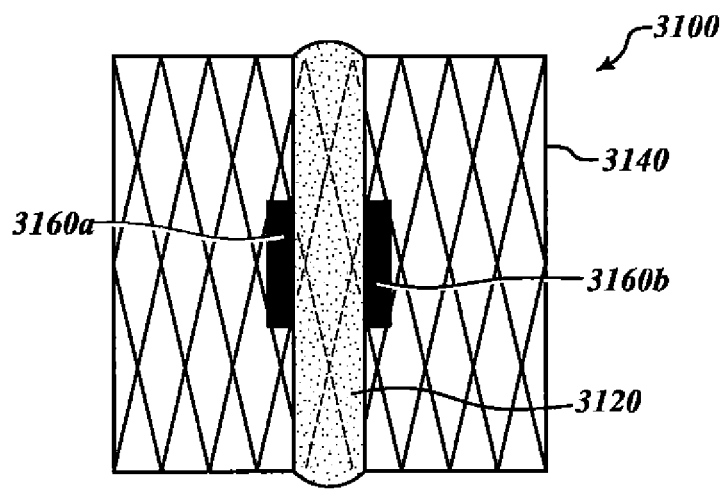
Figure 17:
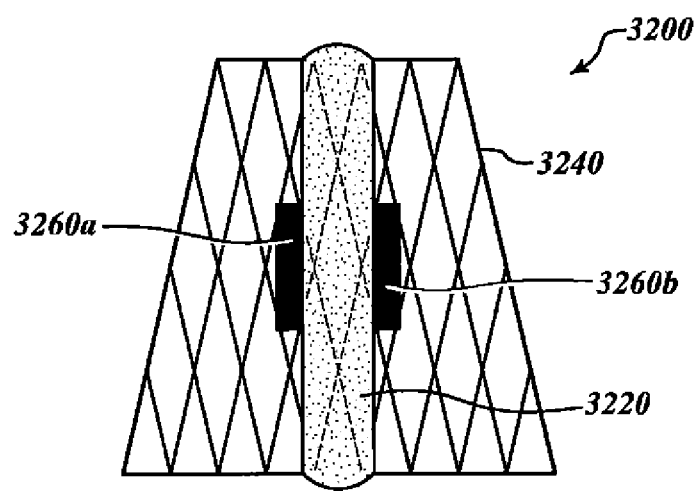

FIGS. 15-17 illustrate agent delivery systems that include stents. The stents in FIGS. 15-17 can be formed of stainless steel, a shape memory material such as Nickel Titanium. Other variations include stainless steel etched stents with porous surface, a coated stainless steel or Nickel Titanium with a porous oxide such as Iridium Oxide or Titanium Oxide, urethanes and poly urethanes, styrene isobutylene styrene. In other examples, the stents could be formed of bioabsorble materials, such as polylactic acid (PLA), poly (lactic-co-glycolic acid) (PLGA), tyrosine-derived polycarbonate, PEG, PLLA, collagen and copolymers of these materials. The stents shown in FIGS. 15-17 can be deployed by any known technique, including balloon assisted expansion, self-expanding stents formed of a shape memory metal, or guide wire assisted deployment. The braided structures discussed below with reference to FIGS. 15-17 can also be replaced by a tubular structure made of, for example, silicone.

The stents can have a length in the range of 10 to 50 mm. The diameter of the stents in a collapsed state can be relatively small. For example, a maximum diameter of the stents in FIGS. 15-17 can be in a range of about 1 mm to about 10 mm when fully collapsed. For example, to treat a bronchial tree of a human, the diameter of the expanded diameter of the stents can be in a range of about 5 mm to about 25 mm.

FIG. 15 illustrates an agent delivery system 4000 that generally includes the stent 4040, an agent delivery portion 4020, and marking elements 4060a and 4060b. As with the basket 3240 in FIG. 13, the agent delivery portion 4020 can include excipients such as polylactide (PLA), its copolymers with glycolide (PLGA), iopromid, urea, shellac and butyryl-trihexyl citrate (BTHC), or non-biodegradable substances such as fluoropolymer or styrene-isobutylene-styrene, or any combination thereof. The stent 4040 could be coated along the open framework that makes up the stent to form the agent delivery portion 4020. In another example, as depicted in FIG. 15, the agent delivery portion 4020 is on a strip of material can be formed of any material that is compatible with the expandable member, such as, for example, polytetrafluoroethylene (PTFE) or urethane, that covers the basket 4040. The strip of material could be fully or partially covered with the agent. As with the previous examples, the agent delivery portion 4020 delivery portion can be sized for positioning between adjacent cartilage rings. Likewise, several axially offset strips or segments of delivery portion 4020 delivery portion could be used.

In this example, the marking elements 4060a and 4060b could be placed on the stent 3040 to aid in identification of the coated portion of the stent 4040 and aid in aligning the agent delivery portion 4020 between adjacent cartilage rings.

FIG. 16 illustrates an agent delivery system 3100 that generally includes a stent 3140, a raised agent delivery portion 3120, and marking elements 3160a and 3160b. The stent 3140 is generally similar to the stent 4040 in FIG. 15, with the exception that the agent delivery portion 3220 is raised to aid in placement of the stent 3140 in a manner similar to the raised agent delivery portion 2220 discussed with reference to FIG. 12. In this example, the raised agent delivery portion 3120 can be a ring that is between 0.5 mm and 4.0 mm in width to facilitate seating between adjacent cartilage rings. The ring can be moveable relative to the stent 3140 to further facilitate placement. Alternatively, the ring can be fixed. In one example, the ring is loosely tethered to the stent 3140 with sutures. In another example, the ring is formed from the same material as the stent, such as, for example, silicone. In yet another example, the ring is integral with the stent.

The raised agent delivery portion 3120 is, in other examples, a band that stays in place due to friction between the band and the stent 3140. Such a raised agent delivery portion 3120 can be expandable together with the stent 3140. In other examples, the band is a thin film that extends at least partially around a circumference of the stent 3140 that is anchored the stent 2240 with several sutures. The thin film can extend entirely around the circumference of the stent 3140.

FIG. 17 illustrates an agent delivery system 3200 that generally includes a stent 3240, a raised agent delivery portion 3220, and marking elements 3260a and 3260b. The stent 3240 is generally similar to the stent 3140 in FIG. 16, with the exception that the stent 3240 includes tapered ends that facilitate placement in, for example, a right main bronchus. The right main bronchus includes a shortened anatomy that does not facilitate the use of longer stents due to the upper right lobe take off. In this example, the tapered ends of the stent 3240 allow an agent to be delivered with the advantage of ensuring that the stent remains in place and does not tip or dislodge.

The stents in FIGS. 15-17 can be permanently implanted in the airway, or removed after a desired period of time. The desired period of time can vary depending on the type of agent employed, the structure of the delivery mechanism on the stent, and that needs of a particular patient, with the overall time a stent is placed in a patient's airway ranging from as short as about one minute to as long as two years.

In some cases, stents are positioned in a patient for relatively short periods of time. As noted above, dwell times for agent coated balloons can range from as short as 30 seconds to as long as 30 minutes. In some patients, it may not be acceptable to block an airway or a portion thereof with a balloon for this amount of time, especially for lower generation airways. For these patients, a temporary stent can be used placed in the airway for as short as a few minutes, to as long as a few weeks. For example, a stent could be placed in a patient for as short as 1 minute to as long as two days. In other examples, the treatment time may last between two days and two months.

In other examples, a stents is positioned in a patient for longer periods of time, ranging from about two months to about two days. In other examples, stents are placed in a patient for between around four months and eight months. In other examples, a stent is removed after about six months in a patient.

In general, the dwell time of the agent delivery device can vary depending upon the type of agent used and the type of agent delivery device, itself. For example, a wire stent can be maintained in-place for a long period of time and can be considered, in some examples, to be permanently implanted.

In other examples, a removable stent can be employed for chronic treatment of the airways. Such a device can be made of a non-embedding material, such as silicone. Such a device can be chronically positioned in the airway for time periods that are in some examples, between one week and two months, in other examples between twenty four hours and three to six months, and in other examples about one month.

In a further example, an agent is applied over a very short time frame. Such agents can be delivered by a balloon that, for example, completely occludes an airway up to about four to five minutes. If a ventilated device is used, such as a ventilated balloon, a short time frame delivery may last as long as about thirty minutes.

In another aspect, advantageously, agents that have higher levels of solubility can be utilized in combination with any of the devices disclosed above. Unlike drug delivery in the blood stream, drug delivery in the airways is not susceptible to solubility concerns associated with immersion in a moving fluid. The table below summarizes the solubility levels of various agents.

12/913,702 filed on Oct. 27, 2010, U.S. application Ser. No. 12/944,666 filed Nov. 11, 2010, U.S. application Ser. No. 13/081,406 filed on Apr. 6, 2011, U.S. Provisional Application No. 61/543,759, and U.S. Provisional Patent Application No. 61/786,203, filed on Mar. 14, 2013.

For example a stent that delivers an agent can be used in combination with an energy delivery device to ensure airway patency during and following treatment as well as improve agent delivery. Certain agents disclosed above, such as sclerosing agent, have the potential to cause damage

| Agent | Solubility in Water (mg/L) | MW | (mol/L) | Part H20/part solute | LogP | Soluble (Y/N) | Extent | Could not determine |
|---|---|---|---|---|---|---|---|---|
| Phenol | 83000 | 94.1 | 0.882040383 | 63.48915663 | 1.46 | Y | sparingly soluble | |
| Ropivacaine | 57.6 | 274 | 0.000210219 | 266388.8889 | | N | insoluble | |
| Ropivacaine HCL | 53800 | 329 | 0.163525836 | 342.4535316 | | Y | slightly soluble | |
| Sodium Tetradecyl sulfate | 50,000 | 316.43 | 0.158012831 | 354.4016 | | Y | slightly soluble | |
| Polidocanol | miscible | | | | | Y | miscible | |
| Ethanol | miscible | | | | −0.235 | Y | miscible | |
| hypertonic dextrose 50% | 1000000 | 180 | 5.555555556 | 10.08 | | Y | freely soluble | |
| ethanolamine oleate | | | | | | | | X |
| Sodium Morrhuate | | | | | | | | X |
| Arsenic | | | | | | N | | |
| Arsenic acid | 170,000 | 142 | 1.197183099 | 46.77647059 | | Y | freely soluble | |
| Nitric Oxide | 85.36 | 30 | 0.002845333 | 19681.34958 | | N | insoluble | |
| Glutonate | | | | | | | | X |
| Lidocaine | 4,100 | 234 | 0.017521368 | 3196.097561 | 2.44 | Y | very slightly soluble | |
| Bupivicaine | 2,400 | 288 | 0.008333333 | 6720 | 3.41 | Y | very slightly soluble | |
| Mepivacaine | 7000 | 246 | 0.028455285 | 1968 | 1.95 | Y | very slightly soluble | |
| Procainamide | 5050 | 271 | 0.018634686 | 3005.148515 | 0.88 | Y | very slightly soluble | |
| Mexiletine | 8250 | 179 | 0.046089385 | 1215.030303 | 2.15 | Y | slightly soluble | |
| Tocainide | 10700 | 192 | 0.055729167 | 1004.859813 | 0.8 | Y | slightly soluble | |
| Tetrodotoxin | | | | | | | | X |
| Tetrodotoxin citrate | 31927 | 319 | 0.100084639 | 559.5264196 | | Y | slightly soluble | |
| Tetraethylammonium | | | | | | N | | |
| Chlorotoxin | | 3997 | 10 | 5.6 | | Y | freely soluble | |
| Ricin | | | | | | Y | soluble | |
| Abrin | | | | | | Y | slightly soluble | |
| Saprin | 10000 | 30,000 | 0.000333333 | 168000 | | N | insoluble | |

According to US Pharmacopea standards, the scale of solubility (part of solvent per part of solute) is as follows:

| | |
|---|---|
| <1 | very soluble |
| 1 to 10 | freely soluble |
| 10 to 30 | soluble |
| 30 to 100 | sparingly soluble |
| 100 to 1000 | slightly soluble |
| 1000 to 10000 | very slightly soluble |
| >10000 | insoluble |

Typically, there is a cutoff of solubility levels of between 1000 to 10000 mg/L for drug delivery in devices used in the blood stream. By contrast, in the airway, agents with much higher solubility levels can be employed.

The shape and structure of a stent can be tailored for effective agent delivery. For example, a stent can include channels that contain an agent, with selectively exposed portions for agent delivery. In another example, a hollow stent is loaded with an agent, and is porous in areas of desired agent delivery. Other stents can include cavities loaded with an agent that are masked with a membrane designed to release the agent in a controlled manner over time.

The agent delivery systems discussed above can be used together with or in addition to energy delivery system, such as those described in U.S. Pat. No. 8,088,127, PCT Application No. PCT/US2010/056424 filed Nov. 11, 2010 (Publication No. WO 2011/060200), U.S. application Ser. No.

indiscriminately as they travel through the airway wall. As this destruction occurs, the stent can maintain the patency of the airway wall. An energy delivery device that delivers, for example, radiofrequency energy, ultrasound energy, microwave energy, or other type of energy to the airway wall can be used while the stent is in place to create scar tissue that will assist with the patency of the airway. Such scar formation may allow for the removal of the stent after a period of time, or, in the case of a bioabsorbable stent, facilitate the patency of the airway even after the structural integrity of the stent diminishes.

In other examples, an energy delivery device can facilitate transport of the agent to the targeted nerves in the airway wall. For example, applying ultrasound energy to an airway wall to which an agent has been applied may drive the agent deeper into the airway, with the mechanical vibrations pushing the agent towards nerve trunks that extend along the airway. In other examples, merely applying heat to the airway wall may increase blood flow, thereby facilitating agent transport within the airway wall. The beneficial effects of heat application and energy delivery could be realized through energy application prior to, during, or even after agent delivery. In some examples, the devices disclosed in the applications discussed above could include the agent delivery portions disclosed herein, or variations thereof. Such energy application systems could employ any of the cooling systems described in U.S. Provisional Patent Application Ser. No. 61/779,371, filed on Mar. 13, 2013, and incorporated herein by reference in its entirety. In other examples, a heated fluid, rather than a chilled fluid, can be circulated to aid in treatment with an agent.

In other examples, the agents disclosed herein can be delivered via either the needle injection or needleless injection devices and methods disclosed in U.S. Pat. No. 8,172,827, the entire contents of which are incorporated herein by reference.

Although the agent delivery systems and various aspects thereof described herein advantageously allow for a compact design that facilitates compatibility with the working channel of a flexible bronchoscope, the aspects described herein are not so limited. For example, as will be readily apparent to one of ordinary skill in the art upon a complete review of the present disclosure, the aspects disclosed herein are also scalable to be compatible with larger working lumens that may or may not be associated with a bronchoscope. Notably, the present disclosure is not limited solely to systems that are delivered via the working channel of a bronchoscope, but also encompasses systems delivered by other means, such as an independent sheath and/or delivery catheter.

The treatment systems and its components disclosed herein can also be used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue, cardiovascular tissue, respiratory tissue, or the like. Access techniques and procedures used to provide access to a target region can be performed by a surgeon and/or a robotic system. Those skilled in the art recognize that there are many different ways that a target region can be accessed.

The delivery devices disclosed herein can be used with guidewires, delivery sheaths, optical instruments, introducers, trocars, biopsy needles, or other suitable medical equipment. If the target treatment site is at a distant location in the patient (e.g., a treatment site near the lung root 24 of FIG. 1), a wide range of instruments and techniques can be used to access the site. The flexible elongated assemblies can be easily positioned within the patient using, for example, steerable delivery devices, such as endoscopes and bronchoscopes, as discussed above, for example, with reference to side-by side delivery of treatment devices and a flexible bronchoscope and delivery through the working channel of a rigid bronchoscope.

Semi-rigid or rigid elongated assemblies can be delivered using trocars, access ports, rigid delivery sheaths using semi-open procedures, open procedures, or other delivery tools/procedures that provide a somewhat straight delivery path. Advantageously, the semi-rigid or rigid elongated assemblies can be sufficiently rigid to access and treat remote tissue, such as the vagus nerve, nerve branches, nerve fibers, and/or nerve trunks along the airways, without delivering the elongated assemblies through the airways. The aspects and techniques disclosed herein can be used with other procedures, such as bronchial thermoplasty.

The various embodiments and aspects described above can be combined to provide further embodiments and aspects. These and other changes can be made to the embodiments in light of the above-detailed description. The aspects, embodiments, features, systems, devices, materials, methods and techniques described herein may, in some embodiments, be similar to any one or more of the embodiments, features, systems, devices, materials, methods and techniques described in U.S. Pat. No. 8,088,127, PCT Application No. PCT/US2010/056424 filed Nov. 11, 2010 (Publication No. WO 2011/060200), U.S. application Ser. No. 12/913,702 filed on Oct. 27, 2010, U.S. application Ser. No. 12/944,666 filed Nov. 11, 2010, U.S. application Ser. No. 13/081,406 filed on Apr. 6, 2011, and U.S. Provisional Application No. 61/543,759. Each of these applications is incorporated herein by reference in its entirety. In addition, the aspects, embodiments, features, systems, devices, materials, methods and techniques described herein may, in certain embodiments, be applied to or used in connection with any one or more of the embodiments, features, systems, devices, materials, methods and techniques disclosed in the above-mentioned applications and patents.

Unless the context requires otherwise, throughout the specification and claims which follow, the word "comprise" and variations thereof, such as "comprises" and "comprising" are to be construed in an open, inclusive sense, that is, as "including but not limited to."

In general, in the following claims, the terms used should not be construed to limit the claims to the specific embodiments and aspects disclosed in the specification and the claims, but should be construed to include all possible embodiments and aspects along with the full scope of equivalents to which such claims are entitled. Accordingly, the claims are not limited by the disclosure.

What is claimed is:

1. A method of delivering an agent to an airway of a patient to treat a pulmonary disorder in the patient, the method comprising:
    positioning a distal end of an elongate member in a treatment location in the airway of the patient, the elongate member including a medication delivery device having an expandable member, a medication delivery portion extending at least partially circumferentially about the expandable member, and a marker element positioned on the expandable member immediately adjacent to the medication delivery portion on each a proximal and distal side thereof;
    at least partially expanding the expandable member;
    positioning the medication delivery portion between two adjacent cartilage rings in an airway wall of the airway, wherein the medication delivery portion protrudes outwardly from immediately adjacent surfaces of the expandable member on opposing sides of the medication delivery portion; and
    positioning the medication delivery portion in contact with the airway wall of the airway while the medication delivery portion is positioned entirely between the adjacent cartilage rings so that an agent coated on the medication delivery portion transfers into the airway wall to affect nerves that run along the airway so as to relieve airway obstruction in at least one airway distal to the treatment location, wherein the agent comprises ribosome-inactivating proteins (RIPs).

2. The method of claim 1, wherein the expandable member is an inflatable balloon, and the at least partially expanding the expandable member includes at least partially filling the balloon with a fluid.

3. The method of claim 2, wherein the positioning the medication delivery portion in contact with the airway wall includes rotating the medication delivery portion between the adjacent cartilage rings.

4. The method of claim 3, wherein the rotating the medication delivery portion includes partially deflating the balloon, then rotating the medication delivery device using the adjacent cartilage rings as a guide, and then inflating the balloon to reposition the medication delivery portion in contact with the airway wall.

5. The method of claim 2, wherein positioning the medication delivery portion between two adjacent cartilage rings includes viewing the medication delivery portion through the balloon with an optical element of a bronchoscope positioned proximal of the balloon.

6. The method of claim 5, wherein viewing the medication delivery portion through the balloon includes directly coupling the optical element of the bronchoscope to a proximal portion of the balloon.

7. The method of claim 2, wherein positioning the medication delivery portion between two adjacent cartilage rings includes viewing the marker elements adjacent the medication delivery portion through the balloon with an optical element of a bronchoscope positioned proximal of the balloon.

8. The method of claim 7, wherein viewing the marker elements through the balloon includes directly coupling the optical element of the bronchoscope to a proximal portion of the balloon.

9. The method of claim 1, wherein positioning a distal end of the elongate member in the treatment location includes advancing the medication delivery device through a working channel of a flexible bronchoscope.

10. The method of claim 9, wherein the working channel of the flexible bronchoscope includes an inside diameter in the range of 1.0 mm to 6.0 mm.

11. The method of claim 1, wherein the expandable member is a stent, and the at least partially expanding the expandable member includes expanding the stent within the airway of the patient.

12. The method of claim 11, further comprising removing the stent from the airway following treatment.

13. The method of claim 12, wherein removing the stent from the airway following treatment includes removing the stent between about one minute and about two years after placing the stent in the airway.

14. The method of claim 13, wherein removing the stent from the airway following treatment includes removing the stent between about four months and eight months after placing the stent in the airway.

15. The method of claim 14, wherein removing the stent from the airway following treatment includes removing the stent about six months after placing the stent in the airway.

16. The method of claim 11, wherein the medication delivery portion is movable relative to the expandable member, and positioning the medication delivery portion between two adjacent cartilage rings includes moving the medication delivery portion relative to the expandable member.

17. The method of claim 11, further comprising pressing a plurality of needles positioned on the medication delivery portion into the airway wall.

18. The method of claim 1, wherein the expandable member is a basket, and the at least partially expanding the expandable member includes expanding the basket in the airway.

19. The method of claim 1, wherein the medication delivery portion comprises a ring that is tethered to the expandable member.

20. The method of claim 19, wherein the medication delivery portion comprises a film material that is tethered to the expandable member via a plurality of sutures.

21. The method of claim 1, wherein the medication delivery portion is molded from the expandable member such that the medication delivery portion is integral with a sidewall of the expandable member.

22. A method of delivering medication to an airway of a patient to treat a pulmonary disorder in the patient, comprising:
    positioning a distal end of an elongate member in a treatment location in the airway of the patient, the elongate member including a medication delivery device having an expandable member, a medication delivery portion extending at least partially circumferentially about the expandable member, and a marker element positioned on the expandable member immediately adjacent to the medication delivery portion on each a proximal and distal side thereof, wherein the medication delivery portion comprises a ring that is tethered to the expandable member, the ring having a nerve-disrupting agent coated thereon;
    at least partially expanding the expandable member;
    positioning the medication delivery portion between two adjacent cartilage rings in an airway wall of the airway, wherein the medication delivery portion protrudes outwardly from immediately adjacent surfaces of the expandable member on opposing sides of the medication delivery portion; and
    positioning the medication delivery portion in contact with the airway wall of the airway while the medication delivery portion is positioned entirely between the adjacent cartilage rings so that the nerve-disrupting agent coated on the medication delivery portion transfers into the airway wall to affect nerves that run along the airway so as to relieve airway obstruction in at least one airway distal to the treatment location.

23. The method of claim 22, wherein the expandable member is an inflatable balloon, and the at least partially expanding the expandable member includes at least partially filling the balloon with a fluid.

24. The method of claim 23, wherein the positioning the medication delivery portion in contact with the airway wall includes rotating the medication delivery portion between the adjacent cartilage rings.

25. The method of claim 24, wherein the rotating the medication delivery portion includes partially deflating the balloon, then rotating the medication delivery device using the adjacent cartilage rings as a guide, and then inflating the balloon to reposition the medication delivery portion in contact with the airway wall.

26. The method of claim 23, wherein positioning the medication delivery portion between two adjacent cartilage rings includes viewing the medication delivery portion through the balloon with an optical element of a bronchoscope positioned proximal of the balloon.

27. The method of claim 26, wherein viewing the medication delivery portion through the balloon includes directly coupling the optical element of the bronchoscope to a proximal portion of the balloon.

28. The method of claim 23, wherein positioning the medication delivery portion between two adjacent cartilage rings includes viewing the marker elements adjacent the medication delivery portion through the balloon with an optical element of a bronchoscope positioned proximal of the balloon.

29. The method of claim 28, wherein viewing the marker elements through the balloon includes directly coupling the optical element of the bronchoscope to a proximal portion of the balloon.

30. The method of claim 22, wherein positioning a distal end of the elongate member in the treatment location includes advancing the medication delivery device through a working channel of a flexible bronchoscope.

31. The method of claim 30, wherein the working channel of the flexible bronchoscope includes an inside diameter in the range of 1.0 mm to 6.0 mm.

32. The method of claim 22, wherein the expandable member is a stent, and the at least partially expanding the expandable member includes expanding the stent within the airway of the patient.

33. The method of claim 32, further comprising removing the stent from the airway following treatment.

34. The method of claim 33, wherein removing the stent from the airway following treatment includes removing the stent between about one minute and about two years after placing the stent in the airway.

35. The method of claim 34, wherein removing the stent from the airway following treatment includes removing the stent between about four months and eight months after placing the stent in the airway.

36. The method of claim 35, wherein removing the stent from the airway following treatment includes removing the stent about six months after placing the stent in the airway.

37. The method of claim 22, wherein the ring is tethered to the expandable member via a plurality of sutures.

* * * * *